(12) United States Patent
Scherer

(10) Patent No.: US 10,004,734 B2
(45) Date of Patent: Jun. 26, 2018

(54) COMPOSITIONS AND METHODS FOR TREATING REBOUND ERYTHEMA ASSOCIATED WITH TOPICAL ALPHA-ADRENERGIC AGONISTS

(71) Applicant: Warren Scherer, Lutz, FL (US)

(72) Inventor: Warren Scherer, Lutz, FL (US)

(73) Assignee: Warren Scherer, Lutz, FL (US)

( * ) Notice: Subject to any disclaimer, the term of this patent is extended or adjusted under 35 U.S.C. 154(b) by 0 days. days.

(21) Appl. No.: 15/415,422

(22) Filed: Jan. 25, 2017

(65) Prior Publication Data

US 2017/0209439 A1 Jul. 27, 2017

Related U.S. Application Data

(60) Provisional application No. 62/388,304, filed on Jan. 26, 2016.

(51) Int. Cl.
| | |
|---|---|
| *A61K 31/4985* | (2006.01) |
| *A61K 31/165* | (2006.01) |
| *A61K 9/06* | (2006.01) |
| *A61K 45/06* | (2006.01) |
| *A61K 9/00* | (2006.01) |

(52) U.S. Cl.
CPC ........ *A61K 31/4985* (2013.01); *A61K 9/0014* (2013.01); *A61K 9/06* (2013.01); *A61K 31/165* (2013.01); *A61K 45/06* (2013.01)

(58) Field of Classification Search
CPC .... A61K 31/4985; A61K 9/0014; A61K 9/06; A61K 31/165; A61K 45/06
USPC ......................................................... 514/249
See application file for complete search history.

(56) References Cited

U.S. PATENT DOCUMENTS

| | | | |
|---|---|---|---|
| 5,910,512 A | 6/1999 | Conant | |
| 6,117,877 A | 9/2000 | Fogel | |
| 6,294,553 B1 * | 9/2001 | Gil | A61K 31/496 514/314 |
| 2003/0082214 A1 | 5/2003 | Williams et al. | |
| 2014/0329874 A1 | 11/2014 | Gil et al. | |

OTHER PUBLICATIONS

International Search Report and Written Opinion corresponding to International Patent Application No. PCT/US15/35745; 12 pages.
Werner et al., Dermatitis medicamentosa: severe rebound erythema secondary to topical brimonidine in rosacea, Dermatology Online Journal, vol. 21, No. 3, Jan. 2015.

* cited by examiner

*Primary Examiner* — Yevgeny Valenrod
(74) *Attorney, Agent, or Firm* — Leason Ellis LLP

(57) ABSTRACT

The present disclosure provides methods and compositions for treating or preventing erythema, including rebound erythema associated with the use of topical alpha-adrenergic agonists. In certain embodiments, an effective amount of a capsaicinoid, such as capsaicin or a pharmaceutically acceptable salt or derivative thereof, is administered to a subject.

9 Claims, 11 Drawing Sheets
(11 of 11 Drawing Sheet(s) Filed in Color)

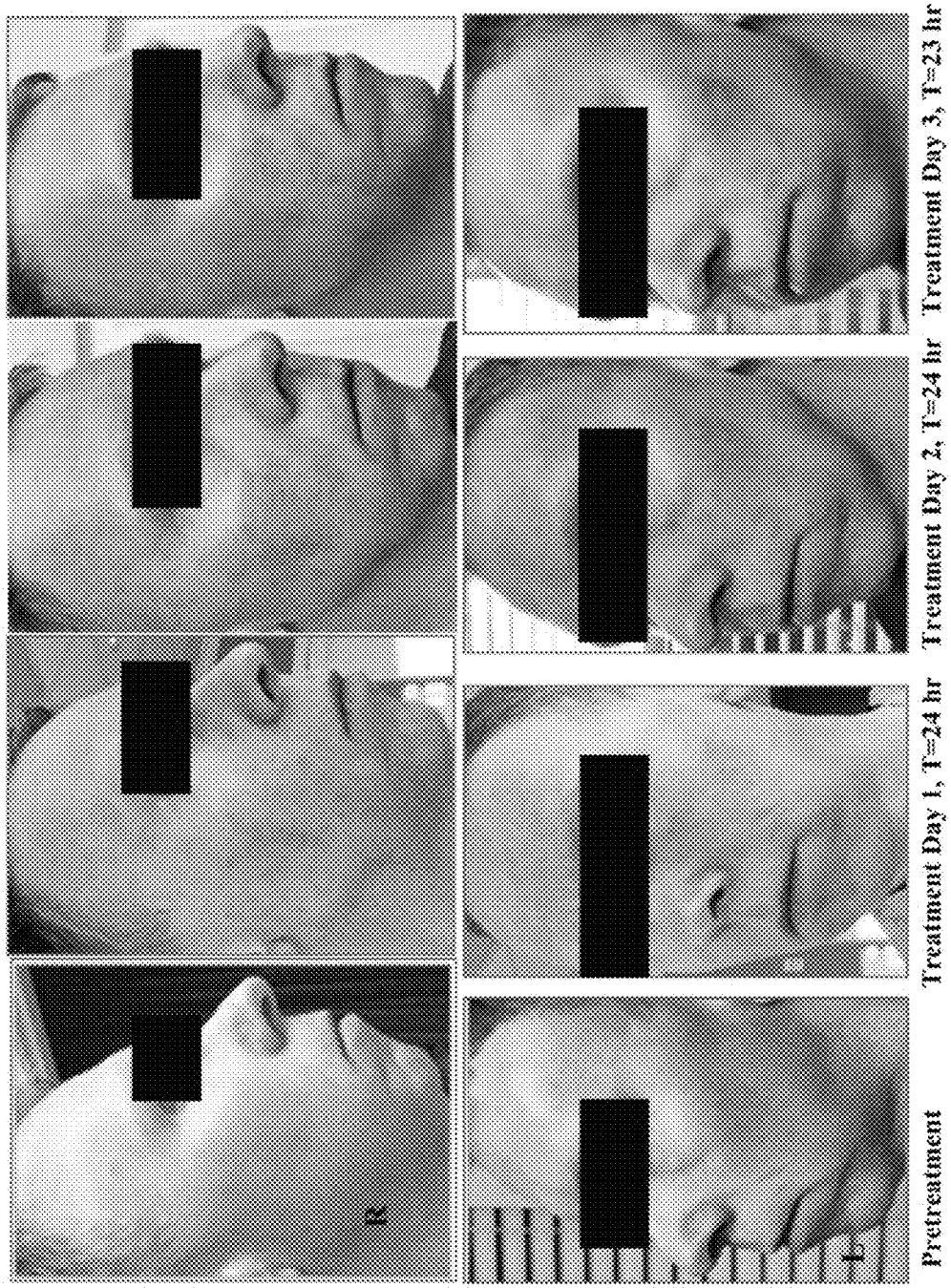

COMPOSITIONS AND METHODS FOR TREATING REBOUND ERYTHEMA ASSOCIATED WITH TOPICAL ALPHA-ADRENERGIC AGONISTS

CROSS-REFERENCE TO RELATED APPLICATIONS

This application claims priority to U.S. Provisional Patent Application No. 62/388,304 filed on Jan. 26, 2016, which is incorporated herein by reference in its entirety.

FIELD OF THE INVENTION

The present invention relates to methods and compositions for treating or preventing rebound erythema associated with the use of topical alpha-adrenergic agonists. In particular, the present invention relates to topically applying a capsaicinoid to treat or prevent rebound erythema.

BACKGROUND OF THE INVENTION

Erythema is a skin condition characterized by redness of the skin. It occurs with skin injury, infection, or inflammation. It can also occur as a reaction to medications, illness or emotions. The causes for some erythema are presently unknown. Currently available treatments for erythema are of limited effectiveness.

Topical alpha-adrenergic agonists are used to treat erythema, typically of the face. Topical brimonidine tartrate, a selective alpha2-adrenergic agonist, is FDA and EMA-approved to treat facial erythema secondary to rosacea under the names Mirvaso® and Onreltea. U.S. Patent Publication Nos. 20050020600, 20160095857 and 20090061020. U.S. Pat. No. 7,439,241. Topical alpha-adrenergic agonists can be used to treat erythema caused by, e.g., rosacea, menopausal flushing, and ingestion of spicy food or alcoholic drinks. In addition, topical alpha-adrenergic agonists are being investigated to treat erythema caused by botulinum toxin (Botox), dermal filler injections, vascularized scars, intense pulsed-light (IPL) laser treatment and daylight-activated photodynamic therapy, as well as injection site erythema caused by biologic medications which are used to treat conditions such as rheumatoid arthritis, multiple sclerosis and other autoimmune diseases. Markus et al., Photo letter to the editor: Topical 0.5% brimonidine gel to camouflage redness of immature scars, J Dermatol Case Rep. 2015 Sep. 30; 9(3): 87-88. Gerber P A, Topical brimonidine tartrate 0.33% gel effectively reduces the post-treatment erythema of daylight-activated photodynamic therapy, Br J Dermatol. 2016; 174 (6):1422-3. Braun et al., Brimonidine tartrate 0.33% gel for the management of posttreatment erythema induced by laser skin resurfacing, J Am Acad Dermatol. 2017; 76(2):e53-e55. Brimonidine tartrate for the treatment of injection related erythema (BRITE), Clinicaltrials.gov, Identifier NCT02568111. Reports have also indicated its effectiveness for capillary hemangiomas in children and as a hemostatic agent in dermatologic surgery. Brimonidine gel is also being investigated for reducing injection site erythema in patients receiving immunomodulatory therapy for multiple sclerosis and as agents for treating certain UV-induced cutaneous neoplasms.

A significant side effect affecting approximately 10-20% of users of topical alpha-adrenergic agonists is late-onset erythema that occurs when the effect of the drug wears off, usually occurring 8 to 24 hours following initial application. Docherty et al., Multidisciplinary Consideration of Potential Pathophysiologic Mechanisms of Paradoxical Erythema with Topical Brimonidine Therapy, Adv Ther. 2016; 33(11): 1885-1895. Werner et al., Dermatitis medicamentosa: severe rebound erythema secondary to topical brimonidine in rosacea, Dermatol Online J, 2015 Jan. 1; 21(3). Tanghetti et al., Optimizing the use of topical brimonidine in rosacea management: panel recommendations, J Drugs Dermatol. 2015 January; 14(1):33-40. This late-onset erythema has also been referred to as "paradoxical erythema", "rebound erythema" or "rebound flushing". It has been suggested that topical alpha-adrenergic agonists cause vasoconstriction and decrease cutaneous blood flow, which in turn reduce cutaneous flushing or erythema. Without being limited to any specific physiological mechanism, it is suggested that after several hours of cutaneous vasoconstriction and limitation of blood flow, both oxygen levels and pH in the skin are reduced. These two conditions can contribute to an increase in the cutaneous levels of substance P, an undecapeptide member of the tachykinin neuropeptide family. Substance P acts to stimulate vasodilation by inducing production of nitric oxide (NO) and causing mast cell degranulation. Ebertz et al., Substance P-induced histamine release in human cutaneous mast cells, J Invest Dermatol. 1987; 88(6):682-5. Hakanson et al., Substance P antagonists release histamine from peritoneal mast cells, Acta Physiol Scand. 1983 February; 117(2):319-20. NO is a potent vasodilator whereas degranulation of mast cells releases histamine, another potent vasodilator.

Capsaicin is the main capsaicinoid in *capsicum* plants including chili peppers. Cordell et al., Capsaicin: identification, nomenclature, and pharmacotherapy. Annals of Pharmacotherapy. 1993: 27:330-336. Capsaicin is known to induce vasodilation and protein extravasation caused by the release of substance P, from axons of unmyelinated C-fibers of sensory nerves. Carpenter et al., Vascular and sensory responses of human skin to mild injury after topical treatment of capsaicin, Br. J. Pharmacol., 1981, 73:755-758. Fitzgerald, Capsaicin and sensory neurons—a review, Pain, 1983, 15: 109-130.

Capsaicin is used clinically as an analgesic in topical ointments, nasal sprays and dermal patches. It is currently marketed for topical administration to treat pain in conditions such as peripheral neuropathy, post-herpetic neuralgia, diabetic neuropathy, osteoarthritis, shingles (herpes zoster), psoriasis, and HIV neuralgia. Martin Hautkappe et al., Review of the Effectiveness of Capsaicin for Painful Cutaneous Disorders and Neural Dysfunction, Clin. J. Pain, 14:97-106, 1998. Capsaicin is also available over the counter to treat minor muscle aches, arthritis and sprains. Topical capsaicin has been found to be safe and effective with little to no systemic absorption.

Capsaicin can elicit erythema and/or an intense burning or stinging sensation upon topical application. Watson et al., A randomized vehicle-controlled trial of topical capsaicin in the treatment of postherpetic neuralgia, Clinical Therapeutics. 15.3 (1993):510-526. Peikert, A. et al., Topical 0.025% capsaicin in chronic post-herpetic neuralgia: efficacy, predictors of response and long-term course, J. Neural. 238: 452-456, 1991; Watanabe, A. et al, Efficacy of capsaicin ointment (Zostrix) in the treatment of herpetic pain and postherpetic neuralgia, Pain Clinic 15:709-713, 1994.

There is a need to reduce late-onset cutaneous erythema associated with the use of topical alpha adrenergic agonists.

SUMMARY

The present disclosure provides for a pharmaceutical composition for topical application. The composition may comprise an effective amount of an alpha-adrenergic agonist and an effective amount of a capsaicinoid.

The pharmaceutical composition may further comprise an effective amount of a neurokinin 1 receptor antagonist and/or a neurokinin 2 receptor antagonist.

The pharmaceutical composition may further comprise a local anesthetic agent.

The present disclosure also provides for a method of treating or preventing rebound erythema. The rebound erythema may be caused by a topical alpha adrenergic agonist. The method may comprise topically applying an effective amount of an alpha-adrenergic agonist and an effective amount of a capsaicinoid to an affected area of the skin of a subject.

Also encompassed by the present disclosure is a method of treating or preventing rebound erythema, the method comprising topically applying a pharmaceutical composition comprising an effective amount of a capsaicinoid to an affected area of the skin of a subject, where the area is affected by the rebound erythema associated with a topical alpha-adrenergic agonist.

The alpha-adrenergic agonist and the capsaicinoid may be applied simultaneously. Alternatively, the capsaicinoid may be applied prior to or after the application of the alpha-adrenergic agonist.

The capsaicinoid and the alpha-adrenergic agonist may be in a composition. The capsaicinoid and the alpha-adrenergic agonist may be in two separate compositions.

The capsaicinoid may be capsaicin, dihydrocapsaicin, nordihydrocapsaicin, homodihydrocapsaicin, homocapsaicin, noninvamide, or combinations thereof. In one embodiment, the capsaicinoid is capsaicin. In another embodiment, the capsaicinoid is trans-capsaicin or nonivamide.

The capsaicinoid may be present in an amount ranging from 0.005% to 0.05% by weight (wt %), from 0.01 wt % to 0.025 wt %, from 0.02 wt % to 0.025 wt %, or about 0.01 wt %, relative to total weight of the composition.

The alpha-adrenergic agonist may be brimonidine, oxymetazoline, tetrahydrozoline, nephazoline, xylometazoline, phenylepherine, methoxamine, mephentermine, metaraminol, desglymidodrine, midodrine, salts thereof, or combinations thereof.

The alpha-adrenergic agonist may be present in an amount ranging from 0.05 wt % to 0.5 wt %, from 0.1 wt % to 0.25 wt %, from 0.1 wt % to 0.15 wt %, from 0.2 wt % to 0.25 wt %, or about 0.1 wt %, relative to total weight of the composition.

In certain embodiments, in the pharmaceutical composition(s), the capsaicinoid is capsaicin, and the alpha-adrenergic agonist is brimonidine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. Transient superficial erythema FIG. 1B. Persistent patchy erythema.

FIG. 2A: Baseline; FIG. 2B: 0.025% Capsaicin, bilateral face; FIG. 2C: 0.010% Capsaicin, bilateral face. 0.01% capsaicin cream produced only transient erythema and a mild feeling of warmth with no burning sensation. L, left face; R, right face.

FIG. 4: Example of progressing rebound erythema (patchy erythematous changes) following daily application of 0.20-0.25% brimonidine gel in vehicle at different time points (pretreatment, Day 1, Day 2 and Day 3).

DETAILED DESCRIPTION

Figures 1A, 1B:
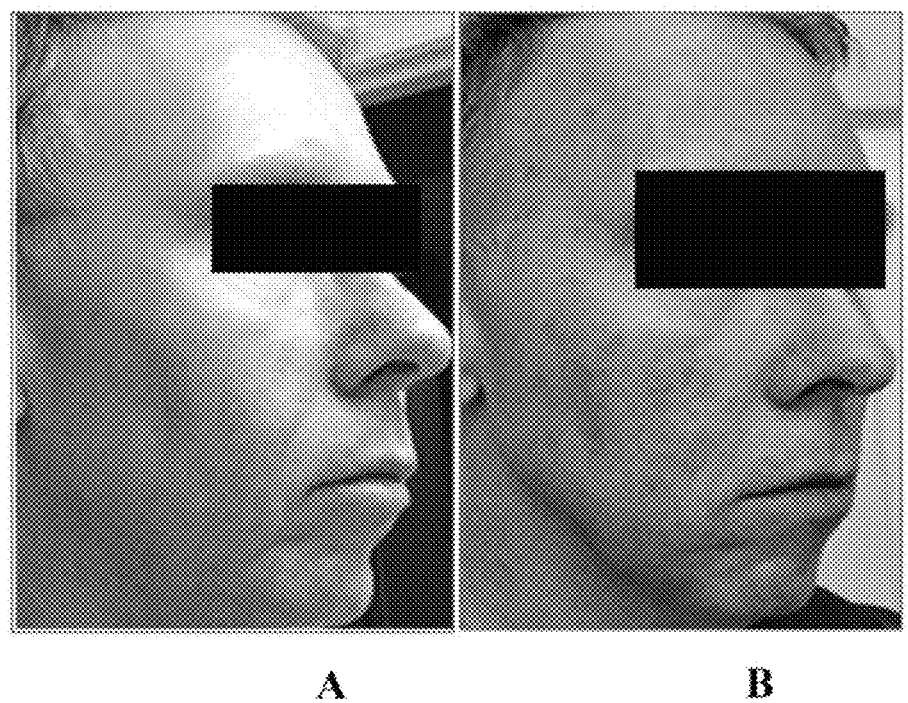
FIGS. 1A-1B: Erythema associated with topical alpha adrenergic agonist use.

The present disclosure provides methods and compositions for treating or preventing erythema, including rebound erythema (or paradoxical erythema, rebound flushing) associated with the use of topical alpha-adrenergic agonists. In certain embodiments, an effective amount of a capsaicinoid, such as capsaicin or a pharmaceutically acceptable salt or derivative thereof, is administered to a subject, e.g., topically. In some embodiments, the pharmaceutical composition contains one or more esters of capsaicin.

In certain embodiments, the present composition comprises an effective amount of a capsaicinoid and an effective amount of an alpha-adrenergic agonist. In one embodiment, the present composition comprises one, two, three or more capsaicinoids.

In certain embodiments, a subject is treated with a capsaicinoid (such as capsaicin), or a pharmaceutically acceptable salt or solvate thereof, or a physiologically functional derivative thereof, via topical, intravenous, oral, transdermal or intranasal administration.

Also encompassed by the present disclosure is a method of treating or preventing rebound erythema. The method may comprise administering (e.g., topically applying) an effective amount of an alpha-adrenergic agonist and an effective amount of a capsaicinoid to a subject (e.g., to an affected area of the skin of a subject). In certain embodiments, the alpha-adrenergic agonist and the capsaicinoid are administered simultaneously. In certain embodiments, the capsaicinoid is administered prior to the administration of the alpha-adrenergic agonist. In certain embodiments, the capsaicinoid is administered after the administration of the alpha-adrenergic agonist. In certain embodiments, the capsaicinoid and the alpha-adrenergic agonist are in a composition. In certain embodiments, the capsaicinoid and the alpha-adrenergic agonist are in two separate compositions.

The present disclosure provides for a method of treating or preventing rebound erythema, the method comprising administering (e.g., topically applying) a pharmaceutical composition comprising an effective amount of a capsaicinoid to a subject (e.g., to an affected area of the skin of a subject, where the area is affected by the rebound erythema associated with a topical alpha-adrenergic agonist).

In certain embodiments, the present composition comprises an effective amount of a substance P antagonist and an effective amount of a topical alpha-adrenergic agonist.

In certain embodiments, erythema, including rebound erythema, is treated or prevented by administering a substance P antagonist to a subject, via topical, intravenous, oral, transdermal or intranasal administration.

The present active agent may be formulated into a cosmetic, pharmaceutical, and/or dermatological composition for treating erythema, including rebound erythema.

The present compositions may be applied topically to the face, the neck, the hair, the mucous membranes and the nails, major folds, or any other area of the body skin.

The compositions of the invention may be administered either via a local route, e.g., topically or by subcutaneous and/or intradermal injection, or via a systemic or general route, e.g., orally and/or by intramuscular injection.

The present agent/composition may be administered therapeutically to achieve a therapeutic benefit ("treating") or prophylactically to achieve a prophylactic benefit ("preventing"). By therapeutic benefit is meant eradication or amelioration of erythema being treated, and/or eradication or amelioration of one or more of the symptoms associated with erythema. By prophylactic benefit is meant prevention or delay of the onset of erythema, including rebound erythema associated with the use of topical alpha-adrenergic agonists, and/or prevention or delay of the onset of one or more of the symptoms associated with erythema, including rebound erythema associated with the use of topical alpha-adrenergic agonists. In certain embodiments, an effective amount of the present agent/composition to be administered prevents erythema (including rebound erythema associated with the use of topical alpha-adrenergic agonists) from developing or being exacerbated into more serious conditions.

"Treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

An effective amount of an agent/drug refers to a therapeutically effective amount or a prophylactically effective amount. A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount. A therapeutically effective amount of a drug is an amount effective to demonstrate a desired activity of the drug. A therapeutically effective amount may vary depending on the compound, the disorder and its severity and the age, weight, physical condition and responsiveness of the subject to be treated. In certain embodiments, an effective amount of a capsaicinoid (such as capsaicin), or a pharmaceutically acceptable salt or solvate thereof, or a physiologically functional derivative thereof, is an amount effective to prevent or delay the onset of erythema, and/or effective to alleviate, one or more of the symptoms of erythema.

In certain embodiments, the present agent, such as a capsaicinoid (e.g., capsaicin), or a pharmaceutically acceptable salt or solvate thereof, or a derivative thereof, is administered in a composition comprising a pharmaceutically acceptable carrier, vehicle, excipient and/or diluent. Also provided herein is a pharmaceutical composition that comprises a capsaicinoid (such as capsaicin), or a pharmaceutically acceptable salt or solvate thereof, or a derivative thereof, and a pharmaceutically acceptable carrier, vehicle, excipient or diluent, for use in the prophylactic and/or therapeutic treatment of erythema. In certain embodiments, the present disclosure relates to compositions for topical application to the human skin.

The compounds used in the present methods include all hydrates, solvates, and complexes of the compounds. In cases in which compounds have unsaturated carbon-carbon double bonds, both the cis (Z) and trans (E) isomers are within the scope of this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds may be in racemic form or as individual enantiomers. The enantiomers can be separated using known techniques, such as those described in Pure and Applied Chemistry 69, 1469-1474, (1997) IUPAC. In cases wherein compounds may exist in tautomeric forms, such as keto-enol tautomers, each tautomeric form is contemplated as being included within this invention whether existing in equilibrium or predominantly in one form.

The present disclosure is also intended to include use of all isotopes of atoms occurring on the compounds disclosed herein. Isotopes include those atoms having the same atomic number but different mass numbers. Isotopically-labeled compounds can generally be prepared by conventional techniques known to those skilled in the art in place of the non-labeled reagents employed.

The compounds of the present disclosure may be a salt. As used herein, a "salt" is a salt of the present compound which has been modified by making acid or base, salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The present methods also encompass administering a physiologically functional derivative of the present compound. As used herein, the term "physiologically functional derivative" refers to a compound (e.g., a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis. Prodrugs are such derivatives, and a discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Capsaicinoid

The present composition may comprise one or more capsaicinoids. Non-limiting examples of capsaicinoids include capsaicin, dihydrocapsaicin, nordihydrocapsaicin, homodihydrocapsaicin, homocapsaicin, and noninvamide. The capsaicinoid may also be a capsaicin derivative, a capsaicin analogue, or a capsaicin congener. In one embodiment, the capsaicinoid is capsaicin USP. In another embodiment, the capsaicinoid is trans-capsaicin. In yet another embodiment, the capsaicinoid is an ester of capsaicin. U.S. Patent Publication No. 20140134261.

In one embodiment, the composition comprises capsaicin (8-methyl-N-vanillyl-6-nonenamide, or N-(4-hydroxy-3-methoxybenzyl)-8-methyl-6-nonenamide) with the following representative structure.

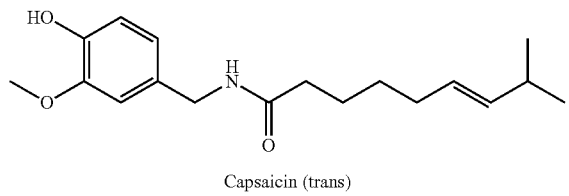 [SMILES: COc1cc(CNC(=O)CCCC/C=C/C(C)C)ccc1O]

Capsaicin (trans)

In certain embodiments, the capsaicin is in a purified form. In certain embodiments, the purified capsaicin used in the present compositions and methods comprise (consist of, or consist essentially of) of the trans isomer (trans-capsaicin). In certain embodiments, the purified capsaicin used in the present compositions and methods comprise (consist of, or consist essentially of) the cis isomer (cis-capsaicin). In certain embodiments, the capsaicinoids in the composition comprise (consist of, or consist essentially of) trans-capsaicin (or cis-capsaicin), e.g., having a purity of greater than about 75% (w/w), greater than about 80% (w/w), greater than about 85% (w/w), greater than about 90% (w/w), greater than about 95% (w/w), greater than about 96% (w/w), greater than about 97% (w/w), greater than about 98% (w/w), or greater than about 99% (w/w) trans-capsaicin (or cis-capsaicin).

The capsaicinoid may be chemically synthesized, or may be of plant, animal, or bacterial origin. For example, capsaicin can be obtained by ethanol extraction of the fruit of *capsicum frutescens* or *capsicum* annum. Capsaicin can also be prepared synthetically. Michalska et al., Synthesis and Local Anesthetic Properties of N-substituted 3,4-Dimethoxyphenethylamine Derivatives, Diss. Pharm. Pharmacol., Vol. 24, (1972), pp. 17-25, (Chem. Abs. 77: 19271a), discloses N-pentyl and N-hexyl 3,4-dimethoxyphenylacetamides which are reduced to the respective secondary amines. U.S. Patent Publication No. 20130303620. U.S. Pat. Nos. 4,997,853; 5,063,060; 5,178,879; 5,296,225; 5,665,378; 6,248,788; 4,599,342; 4,313,958; and 6,239,180. Watson et al., Pain 51: 375-79 (1992); Tandan et al., Diabetes Care 15: 8-13 (1992); Watson et al., Pain 33: 333-40 (1988)), Watson et al., Clin. Ther. 15: 510-26 (1993); Bernstein et al., J. Am. Acad. Dermatol. 21: 265-70 (1989); Morganlander et al., Annals of Neurology 29:199 (1990); Deal et al., Clin. Ther. 13: 383-95 (1991); McCarthy and McCarthy, J. Rheumatol 19: 604-7 (1992); Altman et al., Seminars in Arthritis and Rheumatism 23: 25-33 (1994).

In certain embodiments, a capsaicin analogue or derivative is administered in a therapeutically equivalent amount of capsaicin. In certain embodiments, a capsaicin analogue or derivative is administered at a dose higher or lower than a therapeutically equivalent amount of capsaicin.

Non-limiting examples of capsaicin analogues, congeners and derivatives include, resiniferatoxin (RTX), nonivamide, N-vanillylnonanamides, N-vanillylsulfonamides, N-vanillylureas, N-vanillylcarbamates, N[(substituted phenyl)methyl] alkylamides, methylene substituted N[(substituted phenyl)methyl]alkanamides, N[(substituted phenyl) methyl]-cis-monosaturated alkenamides, N[(substituted phenyl)methyl] diunsaturated amides, 3-hydroxyacetanilide, hydroxyphenylacetamides, pseudocapsaicin, dihydrocapsaicin, nordihydrocapsaicin, homocapsaicin, homodihydrocapsaicin 1, anandamide, piperine, zingerone, warburganal, polygodial, aframodial, cinnamodial, cinnamosmolide, cinnamolide, civamde, olvanil, N-oleyl-homovanillamidia, isovelleral, scalaradial, ancistrodial, beta-acaridial, merulidial, scutigeral, capsinolol, N-arachidonoyldopamine (NADA), and any combinations or mixtures thereof. U.S. Pat. No. 5,962,532.

Substance P Antagonists

The present composition may comprise an effective amount of a substance P antagonist.

Substance P is an eleven-amino acid neuropeptide. In the skin, substance P is released from the terminals of efferent nerve fibers. Following its release, substance P acts on its target tissues by binding to neurokinin (NK) receptors. In cutaneous blood vessels, substance P results in an increase in the activity of the enzyme nitric oxide synthase (NOS). NOS is responsible for producing nitric oxide (NO), a highly potent vasodilator. Additionally, substance P serves as a neuro-immunologic modulator that acts as a mast cell secretogogue in the skin. Substance P stimulates mast cells to release inflammatory mediators such as histamine, another vasodilator. Substance P is involved, in particular, in the transmission of pain and in central nervous system disorders such as anxiety and schizophrenia, in respiratory and inflammatory diseases, in gastro-intestinal diseases, in rheumatic diseases and in certain dermatological diseases such as eczema, psoriasis, urticaria and contact dermatitis. Elbert et al., Substane P-induced histamine release in human cutaneous mast cells, J Invet Dermatol, 1987 88: 682-685. Represent et al., Mast cell activation-a receptor independent mode of substance P action? FEBS Lett 1987, 221 (2):236-240. Peppin et al., Capsaicinoids in the treatment of neuropathic pain, a review, Ther Adv Neurol Disorder, 2014, 7(1):22-32. Anand et al., Topical capsaicin for pain management: therapeutic potential and mechanisms of action of the new concentration 8% patch, Br J Anesth 2011, 107(4): 490-502. Lecci et al., peripheral tachykinin receptors as potential therapeutic targets in visceral diseases, Expert Opin Ther Targets, 2003 7:343-362. Quartera et al., Tachykinin receptor antagonists in clinical trials, Expert Opin Investig Drugs 2009, 18:1843-1864. Malherbe et al., characterization of RO4583298 as a novel potent dual antagonist with in Vito activity at tachykinin NK1 and nK3 receptors, Br J Pharmacol 2011, 162(4):1476-1481. Madaan et al., Neuropeptides: relevance in treatment of depression and anxiety disorders, Drug News Perspective 2009 22(6):319-324. Munoz et al., involvement of substance P and the NK1 receptor in human pathology, Amino Acids 2014 46(7): 1727-1750. Duarte et al., Evidence for involvement of NK3 receptors in the anxiogenic-like effect of SP6-11(c-terminal), a metabolite of substance P, in rats evaluated in the elevated plus-maze, Behav Brain Res 2016 303:168-175.

The substance P antagonists may inhibit or decrease substance P synthesis, inhibit or decrease substance P release, prevent or decrease substance P binding to its receptor, and/or modify (e.g., decrease) substance P activity. In one embodiment, the substance P antagonist elicits an inhibition of the contraction of smooth muscles induced by the administration of substance P.

The substance P antagonist may be a substance P receptor antagonist. In certain embodiments, the present composition may comprise an effective amount of substance P receptor antagonist. In certain embodiments, the composition comprises an effective amount of a neurokinin 1 receptor antagonist and/or a neurokinin 2 receptor antagonist.

The substance P antagonist may be peptides or non-peptide derivatives.

Non-limiting examples of peptide substance P antagonists include sendide and spantide II. U.S. Pat. Nos. 4,472,305 and 4,839,465.

Non-peptide substance P antagonists include, but are not limited to, nitrogen-containing, sulfur-containing or oxygen-containing heterocyclic compounds. The non-peptide substance P antagonists may also be a nitrogen-containing compound containing a nitrogen atom bonded directly or indirectly to a benzene ring. U.S. Pat. Nos. 6,509,014 and 6,235,291. Non-limiting examples of non-peptide substance P antagonists also include a 2-tricyclyl-2-aminoethane derivative, a spirolactarn derivative, a quinuclidine derivative, an azacyclic derivative, an aminopyrrolidine derivative, a piperidine derivative, an aminoazaheterocycle or an isoindole derivative.

Alpha Adrenergic Agonists

Alpha-adrenergic agonists are a class of agents that selectively stimulates alpha adrenergic receptors. There are two subclasses of alpha-adrenergic receptors: alpha-1 and alpha-2.

Non-limiting examples of alpha-adrenergic agonists include, brimonidine, oxymetazoline, tetrahydrozoline, nephazoline, xylometazoilne, phenylepherine, methoxamine, mephentermine, metaraminol, desglymidodrine, midodrine, pharmaceutically acceptable salts thereof, derivatives thereof, and any combinations thereof.

Non-limiting examples of alpha-adrenergic agonists also include clonidine, guanfacine, guanabenz, methyldopa, ephedrine, amphetamine, methydopamine, methamphetamine, lofexidine, moxonidine, dexmedetomidine, mivazerol, methylphenidate, ethylnorepinephrine ritalin, pemoline, methoxamine, phenylephrine, mephentermine, metaraminol, mitodrine, methysergide, ergotamine, ergotoxine, dihydroergotamine, sumatriptan, pharmaceutically acceptable salts thereof, derivatives thereof, and any combinations thereof.

In certain embodiments, the alpha-adrenergic agonist is a (2-imidazolin-2-ylamino)quinoxaline derivative.

In one embodiment, the alpha-adrenergic agonist is brimonidine tartrate.

The representative structure of brimonidine (5-bromo-6-(2-imidazolidinylideneamino)quinoxaline) is shown below.

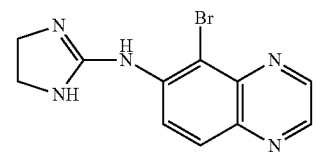

Brimonidine

Oxymetazoline is an alpha-1 adrenergic receptor agonist. The representative structure of oxymetazoline is shown below.

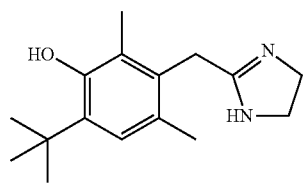

Oxymetazoline

In certain embodiments, the present composition comprises about 0.05% to about 20% by weight, about 0.1% to about 18% by weight, about 0.2% to about 15% by weight, about 0.3% to about 10% by weight, about 0.5% to about 8% by weight, about 0.3%, about 0.4%, about 0.45%, about 0.5%, about 0.55% or about 0.6%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5% or about 10.0%, by weight of one or more alpha-adrenergic agonists (e.g., brimonidine, such as brimonidine tartrate), relative to the total weight of the composition.

Erythema

The present compositions and methods treat and/or prevent erythema and/or a symptom associated therewith.

As used herein, the term "treatment" or "treating" refers to an amelioration, prophylaxis, or reversal of erythema or a symptom associated therewith, for example, by lessening, or delaying the onset of, the redness of the skin affected by the erythema or the symptom.

In certain embodiments, erythema is rebound erythema (also called paradoxical erythema, or rebound flushing) secondary to the use of topical alpha-adrenergic agonists. The rebound erythema may be rebound facial erythema or rebound somatic erythema. The rebound erythema may or may not be increased from the baseline (before being treated by a topical alpha-adrenergic agonist).

In certain embodiments, symptoms associated with erythema include, but are not limited to, flushing, skin-burning sensation and contact dermatitis.

In certain embodiments, erythema is facial erythema, involving cheeks, chin, nose, and/or forehead. Erythema may affect other areas of the body, such as scalp, neck, ears, chest, back, and the eyes. In certain embodiments, erythema is somatic erythema.

Erythema may refer to any skin or mucosal redness, or skin or mucosal irritation, or skin lesions. For example, erythema may include dermatitis (e.g., radiodermatitis), eczema, epitheliolysis, desquamation, redness, rubor, and/or rash. Erythema may also comprise any type of erythema, such as erythema ab igne (EAI), erythema chronicum migrans, erythema induratum, erythema infectiosum, erythema *marginatum*, erythema migrans, erythema multiforme, erythema nodosum, erythema toxicum, keratolytic winter erythema, palmar erythema, Stevens-Johnson syndrome, and toxic epidermal necrolysis (TEN, also known as Lyell's syndrome) and Naevus flammeus nuchae. Erythema may be caused or associated with irradiation, chemotherapy, and/or drug intake (e.g., antibiotics, barbituates, lamotrigine, phenytoin, nonsteroidal anti-inflammatory drugs (NSAIDs); or EGFR inhibitors). In an embodiment, erythema is caused by allergen exposure, such as e.g. various allergens for allergy testing, urushiol, penicillin, latex, or wasp, fire ant and bee stings. In an embodiment, erythema is caused by fungal infection. In an embodiment, erythema is caused by bacterial infection. In an embodiment, erythema is caused by viral infection. In an embodiment, the erythema is caused by a skin disease, which may be psoriasis, atopic eczema, atopic dermatitis (neurodermatitis), eczema, and/or acne. In an embodiment, erythema is caused by a disease affecting internal or external mucosa, e.g. oral, nasal, or intestinal mucosa, and may be selected from the group consisting of inflammatory bowel disease, Morbus Crohn (or Crohn's disease), aphthous stomatitis, conjunctivitis, chronic obstructive pulmonary disease, peptic ulcers, alcohol abuse, and gastritis. In an embodiment, erythema is caused by a somatoform disorder, such as blushing.

Erythema may affect one or more layers of skin or mucosa, e.g. one or more layers of the epidermis and/or one or more layers of the dermis; or one or more layers of the mucous membranes, e.g. the mucosal epithelium (Lamina epithelialis mucosae) and/or the Lamina propria or the conjunctive tissue (e.g. sclera; conjunctiva of the eye).

As used herein, "erythema or a symptom associated therewith" is intended to encompass any type or classification of abnormal skin redness. Erythema may be caused by or associated with, e.g., rosacea, menopausal flushing, ingestion of spicy food, caffeine intake, ingestion of alcoholic drinks, temperature changes, botulinum toxin (Botox) injection, or dermal filler injections. Erythema may also be injection site erythema caused by biologic medications which are used to treat conditions such as rheumatoid arthritis, multiple sclerosis and other autoimmune diseases.

In certain embodiments, the present compositions and methods treat and/or prevent late-onset erythema secondary to the use of topical alpha-adrenergic agonists. This late-onset erythema has also been referred to as rebound erythema, paradoxical erythema, or rebound flushing. Rebound erythema may occur about 2 hours to about 1 week, about 2 hours to about 6 days, about 2 hours to about 5 days, about 2 hours to about 4 days, about 2 hours to about 3 days, about 2 hours to about 48 hours, about 3 hours to about 36 hours, about 4 hours to about 30 hours, about 5 hours to about 24 hours, about 6 hours to about 24 hours, about 7 hours to about 24 hours, about 8 hours to about 24 hours, about 9 hours to about 24 hours, about 10 hours to about 24 hours, about 11 hours to about 24 hours, about 12 hours to about 24 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours, after initial application of a topical alpha-adrenergic agonist (which may be a single treatment, or a first or later treatment in a course of several subsequent treatments).

Rebound erythema may last about 30 minutes to about 4 weeks, about 1 hour to about 3 weeks, about 2 hours to about 2 weeks, about 2 hours to about 1 week, about 2 hours to about 6 days, about 2 hours to about 5 days, about 2 hours to about 4 days, about 2 hours to about 3 days, about 2 hours to about 48 hours, about 3 hours to about 36 hours, about 4 hours to about 30 hours, about 5 hours to about 24 hours, about 6 hours to about 24 hours, about 7 hours to about 24 hours, about 8 hours to about 24 hours, about 9 hours to about 24 hours, about 10 hours to about 24 hours, about 11 hours to about 24 hours, about 12 hours to about 24 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In one embodiment, rebound erythema may temporally resolve with reapplication of topical brimonidine. However, rebound erythema may quickly return and may become progressively worse with repeated applications of topical brimonidine. In one embodiment, rebound erythema may be persistent, patchy erythema. In one embodiment, rebound erythema resolves over several days after topical brimonidine is discontinued.

In certain embodiments, erythema is associated with or resulting from rosacea, e.g., erythema or a symptom associated therewith in a patient with rosacea. A major symptom of rosacea is erythema, generally affects the cheeks, nose, chin, and/or forehead of a patient.

Erythema or a symptom associated therewith encompasses different degrees or grades of erythema or a symptom associated therewith, from mild to severe.

In view of the present disclosure, a skin area that is affected by erythema or that is prone to be affected by erythema can be identified using any diagnostic signs or means known in the art, and can be treated by methods according to the present composition and method.

The present compositions and methods may elicit a marked decrease in skin redness, or complete disappearance of skin redness. For example, the present compositions and methods may result in significant restoration of the skin color to that before the occurrence of late-onset erythema due to administration of a topical alpha-adrenergic agonist.

In certain embodiments, the skin area (e.g., affected by erythema or on which a topical alpha-adrenergic agonist is applied) returns to its baseline level of erythema between applications of the present agents or present compositions.

Erythema or a symptom associated therewith may be assessed by any suitable systems.

For example, erythema or a symptom associated therewith can be rated by a clinician based on Clinician's Erythema Assessment Score (CEA) on a scale from 0 to 4, with 0 being clear skin with no signs of erythema; 1 being almost clear, slight redness; 2 being mild erythema, definite redness; 3 being moderate redness; and 4 being severe redness. See Table 1. Fowler et al., Once-daily topical brimonidine tartrate gel 0.5% is a novel treatment for moderate to severe facial erythema of rosacea: results of two multicentre, randomized and vehicle-controlled studies, Br. J. Dermatol. 2012, 166(3):633-41.

TABLE 1

Clinician's Erythema Assessment Score (CEA)

| Scores | CEA |
| --- | --- |
| 0, Clear | Clear skin with no signs of erythema |
| 1, Almost clear | Almost clear; slight redness |
| 2, Mild | Mild erythema; definite redness |
| 3, Moderate | Moderate erythema; marked redness |
| 4, Severe | Severe erythema; fiery redness |

Erythema or a symptom associated therewith can also be rated by a patient based 153 on Patient's Self Assessment (PSA) on a scale from 0 to 4, with 0 being no redness; 1 being very mild redness; 2 being mild redness; 3 being moderate redness, and 4 being severe redness.

In certain embodiments, the erythema is of grade 0 or higher, grade 1 or higher, grade 2 or higher, grade 3 or higher, or grade 4 or higher, as evaluated by CEA, PSA or the combination of CEA and PSA. In one embodiment, the erythema is of grade 0 to 1, grade 0 to 2, grade 0 to 3, grade 0 to 4, grade 1 to 2, grade 1 to 3, grade 1 to 4, grade 2 to 3, grade 2 to 4, or grade 3 to 4, as evaluated by CEA, PSA or the combination of CEA and PSA.

The efficacy of the treatment can be measured using methods known in the art. For example, the efficacy can be measured by the grades of improvement as evaluated by CEA, PSA or the combination of CEA and PSA, and the duration of the improvement. According to an embodiment, the present composition and method results in noticeable effect, e.g., at least 1-grade improvement, at least 2-grade improvement, at least 3-grade improvement, at least 4-grade improvement, about 1-grade improvement, about 2-grade improvement, about 3-grade improvement, or about 4-grade improvement, of the erythema or the symptom as evaluated by CEA, PSA or the combination of CEA and PSA, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 1 hour, about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 14 hours, within about 16 hours, within about 18 hours, within about 20 hours, within about 22 hours, within about 24 hours, within about 2 days, within about 3 days, within about 4 days, within about 5 days, within about 6 days, or within about 7 days, after the initial, second, third or subsequent application of the present agent or composition.

In certain embodiments, the noticeable effect may progress to maximum improvement, which includes a 1-grade improvement, a 2-grade improvement, a 3-grade improvement, or a 4-grade improvement, of the erythema or the symptom (as evaluated by CEA, PSA or the combination of CEA and PSA) that lasts for a sustained period of time, such as lasting about 30 minutes to about 4 weeks, about 1 hour to about 3 weeks, about 2 hours to about 2 weeks, about 2 hours to about 1 week, about 2 hours to about 6 days, about 2 hours to about 5 days, about 2 hours to about 4 days, about 2 hours to about 3 days, about 2 hours to about 48 hours, about 3 hours to about 36 hours, about 4 hours to about 30 hours, about 5 hours to about 24 hours, about 6 hours to about 24 hours, about 7 hours to about 24 hours, about 8 hours to about 24 hours, about 9 hours to about 24 hours, about 10 hours to about 24 hours, about 11 hours to about 24 hours, about 12 hours to about 24 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. The maximum improvement may or may not decline to noticeable effect, which may then disappear.

In certain embodiments, the present composition and method result in significantly more effective treatment of the erythema and the symptom than a vehicle control for reduction of erythema as measured by a 12-hour success profile evaluated on both CEA and PSA scales, without causing any unacceptable adverse effect. In one embodiment, the 12-hour success profile comprises at least 1-grade improvement, at least 2-grade improvement, at least 3-grade improvement, at least 4-grade improvement, about 1-grade improvement, about 2-grade improvement, about 3-grade improvement, or about 4-grade improvement, of the erythema or the symptom as evaluated by CEA, PSA or the combination of CEA and PSA.

In certain embodiments, the present composition and method result in significantly more reduction of erythema compared to a vehicle control as measured by a 12-hour success profile evaluated on both CEA and PSA scales, without causing any unacceptable adverse effect. U.S. Patent Publication No. 20160095857.

In certain embodiments, the 12-hour success profile comprises a noticeable effect of 1-grade improvement of the erythema or the symptom, and/or about 1 hour to about 8 hours of a 2-grade improvement of the erythema or the symptom. In certain embodiments, the 2-grade improvement lasts, for example, at least about 6 hours, at least about 5 hours, at least about 4 hours, at least about 3 hours, at least about 2 hours or at least about 1 hour.

In certain embodiments, the 12-hour success profile comprises a noticeable effect of 1-grade improvement of the erythema or the symptom and about 2 hours to about 7 hours of a 2-grade improvement of the erythema or the symptom.

In certain embodiments, the 12-hour success profile comprises a noticeable effect of 1-grade improvement of the erythema or the symptom and about 3 hours to about 6 hours of a 2-grade improvement of the erythema or the symptom.

In certain embodiments, the 12-hour success profile comprises a noticeable effect of 1-grade improvement of the erythema or the symptom and about 2 hours to about 5 hours of a 2-grade improvement of the erythema or the symptom.

Other methods may be used to assess erythema. For example, chromameters have been utilized for analyzing hemoglobin, since skin or mucosal erythema is primarily due to vasodilation and local increases in hemoglobin concentration. Spectrophotometers have also been used for analyzing hemoglobin based on diffuse reflectance spectroscopy, according to which the reflected light from skin is collected and analyzed into its spectral components. Spectral analysis algorithms have been used to calculate chromophore concentrations including oxy- and deoxy-hemoglobin (relating to erythema). Various light reflectance devices such as a Mexameter are also known for giving an erythema index. The analysis of digital color images of skin has also been utilized for analyzing erythema. U.S. Pat. No. 8,150,501. U.S. Patent Publication No. 2005/030372. Jung et al, 2005, Lasers in Surgery and Medicine, 37:186-191. Another imaging analysis tool for the assessment of erythema is the DermaVision system from OptoBioMed. Hirotsugu (The Journal of Medical Investigation, 1998, 44: 121-126) discloses methods for use in measurement of skin color.

In one embodiment, photographs are taken at baseline, before each treatment session, and at different time points after the treatment. At least two dermatologists assess the clinical improvement in the severity of erythema using a quartile grading scale [0, 0-25% improvement (poor); 1, 26-50% improvement (fair); 2, 51-75% improvement (good); and 3, 76-100% improvement (excellent)]. Kim et al., British J. of Dermatology, 2011, 164(3):573-579. Patients are asked about their overall rates of satisfaction using a 10-point visual analog scale (VAS: 0, lowest; and 10, highest). Liu et al., Journal of Cosmetic and Laser Therapy, 2014, early oneline: 1-4.

In one embodiment, the primary efficacy endpoint was "success", defined as a two-grade improvement in both the Clinician's Erythema Assessment (CEA) and the Patient's Self-Assessment (PSA) on selected time points after the start of the application of the present composition. Onset of action may also be evaluated. The secondary efficacy endpoint, a one-grade improvement in CEA and PSA at a selected time point(s) after the start of the application of the present composition.

Erythema can be assessed by methods for analyzing skin color based on measuring the light reflectance of a skin or mucosal area and analyzing the measurement by using a formula to calculate the erythema value. The skin redness or erythema value provides an objective, continuous measure for skin redness or erythema over the entire range of intensities. Accordingly, the higher the skin redness erythema value the higher is the intensity of erythema. U.S. Patent Publication No. 20170000406.

Erythema or skin redness at various time points may be assessed. Erythema or skin redness may be evaluated at various time points before and after the start of treatment by the present composition (e.g., comprising a capsaicinoid). In certain embodiments of the present methods, erythema or skin redness may be assessed prior to the start of treatment by a topical alpha-adrenergic agonist, after the start of treatment by a topical alpha-adrenergic agonist, before the start of treatment by the present composition (e.g., comprising a capsaicinoid), and/or after the start of treatment by the present composition (e.g., comprising a capsaicinoid).

A baseline erythema value may be obtained prior to the start of treatment by a topical alpha-adrenergic agonist, or at the beginning of treatment by a topical alpha-adrenergic agonist (which may be a first treatment in a course of several subsequent treatments). Erythema may be assessed at two or more time-points prior to treatment by a topical alpha-adrenergic agonist, and an according mean baseline erythema value may be calculated.

After the start of treatment by a topical alpha-adrenergic agonist and before the start of treatment by the present composition (e.g., comprising a capsaicinoid), erythema values may be obtained at 1, 2, 3, 4, 5, 6, 7, 8 or more time-points. The one or more erythema values may be defined as initial erythema values and/or rebound erythema values.

After the start of treatment by the present composition (e.g., comprising a capsaicinoid), erythema values may be obtained at 1, 2, 3, 4, 5, 6, 7, 8 or more time-points. The one or more erythema values may be defined as treated erythema values. Erythema or skin redness may be assessed at one or more time-points within and/or after the period of administration of the present composition. For example, erythema or skin redness may be assessed at one or more time-points after a single administration or repeated administrations of the present composition. Erythema or skin redness may be assessed at one or more time-points after the administration of the present composition, i.e., when the present composition is no longer administered.

The gradient between two or more of said erythema values may be determined, e.g. between two or more subsequent measurements or erythema values, or between two or more measurements or erythema values over treatment or observation time. An increase of the erythema value between two or more erythema values over time indicates progression of erythema. No significant change of the erythema value between two or more erythema values over time indicates a stable skin or mucosal condition, i.e., that the composition does not cause erythema, is effective in preventing erythema, is not effective in treating erythema, and/or is not effective in ameliorating the appearance of erythema. A decrease of the erythema value between two or more erythema values over time indicates regression of erythema, i.e., that the composition is effective in treating erythema, or in ameliorating the appearance of erythema.

In one embodiment, the skin or mucosal area is a skin area. In another embodiment, the skin or mucosal area is a mucosal area. The mucosal area may be an external or internal mucosa, e.g. nasal, oral, intestinal mucosa.

In certain embodiments, the skin or mucosal area is a gross area comprising one or more segment areas. The erythema value or any other skin color value may be calculated separately for each subarea. If the light reflectance of a skin or mucosal area is measured by obtaining an image, a subarea may also be a single pixel of the image, i.e., the erythema value is calculated for one or more single pixels. Accordingly, a mean erythema value or a mean value of any other skin color value may be calculated of one or more single pixels of the image, the gross area, and/or the segment area.

The segment area may be an erythema area (or a representative part of an erythema area). In one embodiment, the erythema area is an area being prone to erythema, which may e.g. be caused by a disease and/or treatment as described herein. In another embodiment, the erythema area is an area characterized by erythema. The treatment may be local (topical) or systemic. Accordingly, in an embodiment, the segment area prone to erythema or characterized by erythema may be the analyzed treatment area of a local treatment, or the analyzed area at which the erythema occurs upon systemic treatment. The analyzed segment area may also be a treatment area (or a representative part of a treatment area), i.e. an analyzed area that is or will be treated, e.g. with the present composition. In one embodiment, the analyzed erythema area is also a treatment area.

The analyzed segment area may also be a reference area (or a representative part of a reference area). The reference area may be an area of the same subject. In an embodiment, the reference area may be an area of one or more subjects other than the subject to be assessed. Said different subjects may be of the same race, of the same or similar skin color, and/or of the same skin type (e.g., according to the Fitzpatrick Skin Scale). In an embodiment, these different subjects have the same kind of skin condition, e.g., erythema. In still another embodiment, these different subjects suffer from the same or a similar disease and/or undergo the same or similar treatment. Accordingly, a reference curve of two or more reference erythema values may be generated for comparison to the subject's measurements. In general, for any comparison of erythema values (e.g., to reference values), the area under the curve between two or more erythema values may be determined and compared to, e.g., the area under the curve of two or more reference erythema values.

The reference area may be an area similar to the erythema and/or treatment area, i.e. an area of the same or a similar region of the body, and/or of the same or similar nature (e.g. of similar color and/or shape). In one embodiment, the reference area is adjacent to the segment area to be compared to, e.g. the erythema and/or treatment area. In one embodiment, the reference area is of the same size as the segment area to be compared to, e.g. the erythema and/or treatment area. The erythema value calculated for a reference area may also be called reference erythema value.

In one embodiment, the reference area is not characterized by erythema, i.e., is free from erythema. For example, the reference area may be the treatment area prior to treatment with a topical alpha-adrenergic agonist, thus, prior to development of rebound erythema. The reference area may be the treatment area prior to treatment with the present composition. In one embodiment, the reference area is not a treatment area. In an example, the reference area is left completely untreated. In a further embodiment, the reference area is treated with a placebo or with a reference treatment, such as, the gold standard treatment or a comparative product. In another embodiment, the reference area is characterized by erythema (e.g., rebound erythema), as the present composition and method can ameliorate erythema (e.g., rebound erythema). In another embodiment, the reference area is an erythema and/or treatment area prior to development of erythema and/or prior to treatment. The reference erythema value calculated for a reference area that is an erythema and/or a treatment area, but based on a measurement prior to development of erythema and/or prior to treatment, may also be called baseline erythema value or initial erythema value.

In an embodiment, the erythema value is compared to a reference erythema value. For example, the erythema value of a segment area (e.g. a treatment and/or erythema area) is compared to one or more reference erythema values. In one embodiment, the reference erythema value is calculated based on one or more reference areas. In another embodiment, the reference erythema value is the erythema value of the same segment area from which the follow-up erythema value is calculated, e.g. an erythema and/or treatment area, assessed prior to treatment and/or development of erythema.

In another embodiment, the erythema value may be compared to more than one reference erythema values and/or one or more reference gradients between two or more erythema values of reference areas. Said reference erythema values and/or reference gradients may include reference erythema values of the same subject or of one or more different subjects. For example, a reference erythema gradient, or a rating or reference curve may be determined from subjects with the same or similar type and/or grade of erythema, e.g. with the same disease or treatment. Accordingly, the erythema of a subject may be assessed by calculating one or more erythema values and comparing the one or more erythema values to one or more reference erythema values, a reference erythema gradient between two or more reference erythema values, and/or to a rating or reference curve.

The measurement or image may be obtained by any suitable measurement method or imaging method, such as e.g. spectrophotometry, video, video frame buffer, and/or photography. For example, the measurement or image may be obtained by a method not requiring any direct contact with the gross area and/or segment areas, e.g. photography. In an embodiment, the measurement or image is obtained by spectrophotometry and/or photography. In an embodiment, the measurement or image is obtained by digital photography. The measurement or image may also be obtained by using endoscopic devices. In one embodiment, the skin or mucosal area is an internal mucosal area and the light reflectance is measured by endoscopic methods.

For example, the erythema value may be converted into a relative value compared to the respective maximal value, which is set to 100%, in order to compare several erythema values based on different measurement methods or imaging methods, and/or based on different color depths.

In one embodiment, the methods of the invention are repeated at several time-points, e.g. at one or more time-points prior to, during, and/or after treatment, development, and/or amelioration of erythema.

In particular, the light reflectance of a skin or mucosal area of a subject may be measured at one or more time-points prior to, during, and/or after development or progression of erythema, or prior to, during, and/or after amelioration or regression of erythema, or prior to, during, and/or after the period of administration of the pharmaceutical preparation, or prior to, during, and/or after the period of treatment (e.g. a local treatment of the skin or mucosal area, or a systemic treatment of the subject). The gradient between two or more of said erythema values may be determined, e.g. between two or more subsequent measurements or erythema values, or between two or more measurements or erythema values over treatment or observation time. Accordingly, the erythema value calculated based on a measurement taken prior to any treatment (e.g. radiation) and/or manifestation of erythema may be the baseline erythema value. Any erythema value calculated based on a measurement taken during or after any treatment (e.g. radiation) and/or manifestation of erythema may be a follow-up erythema value.

Combination with Other Active Agents

The present agent (e.g. a capsaicinoid and/or a substance P antagonist) or composition may be administered to the subject simultaneously with, before, after, or in a sequence and within a time interval of, the administration of a topical alpha-adrenergic agonist (e.g., brimonidine etc. as described herein), such that the present agent or composition can act together to treat or prevent erythema and symptoms associated therewith (e.g., rebound erythema). For example, the present agent (e.g., a capsaicinoid and/or a substance P antagonist) or composition and a topical alpha-adrenergic agonist (e.g., brimonidine etc. as described herein) can be administered in the same or separate formulations at the same time or different times. In certain embodiments, the present agent (e.g., a capsaicinoid) or composition can be administered before or after the administration of a topical alpha-adrenergic agonist (e.g., brimonidine).

By co-administration it is meant either the administration of a single composition containing both the present agent (e.g., a capsaicinoid) and a topical alpha-adrenergic agonist, or the administration of the present agent (e.g., a capsaicinoid) and a topical alpha-adrenergic agonist as separate compositions within short time periods.

The present agent (e.g., a capsaicinoid) can be combined and administered with a topical alpha-adrenergic agonist in separate compositions. In certain embodiments, the separate compositions are administered simultaneously. In certain embodiments, the separate compositions are not administered simultaneously, such as, for example, in a sequential manner.

The present compound or composition may be administered to a subject alone, or may be administered to a subject in combination with one or more other treatments/agents (a second agent).

In certain embodiments, the second agent is a local anesthetic, a nonsteroidal anti-inflammatory agents (NSAID), an antihistamine, an antibiotic, a nitric oxide synthase (NOS) inhibitor, a corticosteroid, acetaminophen, a vasoconstrictor, a vasodilator, a sodium channel blocker, or combinations thereof. U.S. Patent Publication No. 20090117167.

In certain embodiments, the present compound or composition is administered to a subject in combination with one or more treatments/agents such as corticosteroids, NMDA antagonists, an inhibitor of nitric oxide synthesis (e.g., NG-nitro-L-arginine methyl ester (L-NAME) or $N^G$-nitro-L-arginine (L-NOARG) etc.), opioid agonists and/or antagonists.

In certain embodiments, the present compound or composition is administered to a subject in combination with one or more treatments/agents such as, a topical H-1 histamine receptor antagonist, a mast cell stabilizer (e.g., olopatadine etc.), an antibacterial agent, an anthelmintic agent, an anti-angiogenesis agent, a steroidal anti-inflammatory agent, a non-steroidal anti-inflammatory agent, an antioxidant or derivatives of retinoic acid, as well as halogens.

In some embodiments, the second agent is one or more nonsteroidal anti-inflammatory agents (NSAIDs). NSAIDs include, but are not limited to, salicylates such as aspirin (acetylsalicylic acid), diflunisal, salsalate, salicylic acid, acetylsalicylate, methylsalicylate, methyl acetylsalicylate, trolamine salicylate and lysine salicylate; p-amino phenol derivatives such as paracetamol and phenacetin; propionic acid derivatives such as ibuprofen, naproxen, fenoprofen, ketoprofen, dexketoprofen, flurbiprofen, oxaprozin and loxoprofen; acetic acid derivatives such as indomethacin, sulindac, etodolac, ketorolac, diclofenac and nabumetone; enolic acid (oxicam) derivatives such as piroxicam, meloxicam, tenoxicam, droxicam, lornoxicam and isoxicam; and fenamic acid derivatives (fenamates) such as mefenamic acid, meclofenamic acid, flufenamic acid and tolfenamic acid.

In some embodiments, the second agent is one or more corticosteroids. Corticosteroids include, but are not limited to alclometasone dipropionate, amcinonide, amcinafel, amcinafide, beclamethasone, betamethasone, betamethasone dipropionate, betamethasone valerate, budesonide, clobetasone propionate, chloroprednisone, clocortelone, cortisol, cortisone, cortodoxone, difluorosone diacetate, descinolone, desonide, defluprednate, dibydroxycortisone, desoximetasone, dexamethasone, deflazacort, diflorasone diacetate, dichlorisone, esters of betamethasone, flucetonide, flucloronide, fluorocortisone, flumethasone, flunisolide, fluocinonide, fluocinolone acetonide, flucortolone, fluperolone, fluprednisolone, fluroandrenolone acetonide, fluocinolone acetonide, flurandrenolide, fluorametholone, fluticasone propionate, hydrocortisone, hydrocortisone butyrate, hydrocortisone valerate, hydrocortamate, medrysone, meprednisone, methylprednisone, methylprednisolone, mometasone furoate, paramethasone, prednisone, prednisolone, prednidone, triamcinolone acetonide, and triamcinolone.

In some embodiments, the second agent is one or more NMDA antagonists. Examples of NMDA antagonists include, but are not limited to dextromethorphan and dextrorphan.

In some embodiments, the second agent is one or more opioid agonists and/or antagonists. Examples of opioid agonists/antagonists include but are not limited to purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives.

In some embodiments, the second agent is an inflammation mediator antagonist Exemplary inflammation mediator antagonists include, but are not limited to, diethylenediamine derivatives such as cinnarizine and cyclizine; aminopropane derivatives (dexchlorpheniramine, triprolidine); phenothiazine derivatives (alimemazine, promethazine); auranofin; lisophyline; A802715; sulfasalazine; cetirizine HCl; loratidine; esbatine; setastine HCl.

Non-limiting examples of compounds that can be administered in combination with the present compound or composition include, (a) agents which modify skin differentiation and/or proliferation and/or pigmentation, such as retinoic acid and isomers thereof, retinol and its esters, vitamin D and derivatives thereof, estrogens such as estradiol, kojic acid or hydroquinone; (b) antibacterial agents such as clindamycin phosphate, erythromycin or antibiotics of the tetracycline family; (c) antiparasitic agents, such as metronidazole, crotamiton or pyrethroids; (d) antifungal agents, such as compounds belonging to the imidazole family (e.g., econazole, ketoconazole or miconazole or salts thereof), polyene compounds, such as amphotericin B, compounds of the allylamine family such as terbinafine; (e) steroidal anti-inflammatory agents, such as hydrocortisone, betamethasone valerate or clobetasol propionate, or non-steroidal anti-inflammatory agents, such as ibuprofen and its salts, diclofenac and its salts, acetylsalicylic acid, acetaminophen or glycyrrhetinic acid; (f) anesthetics such as lidocaine hydrochloride and derivatives thereof; (g) antipruriginous agents such as thenaldine or trimeprazine; (h) antiviral agents such as acyclovir; (i) keratolytic agents such as alpha- and beta-hydroxycarboxylic acids or beta-ketocarboxylic acids, their salts, amides or esters and more particularly hydroxy acids such as glycolic acid, lactic acid, salicylic acid, citric acid and fruit acids in general, and derivatives of salicylic acid such as 5-n-octanoylsalicylic acid; (j) anti-free-radical agents, such as alpha-tocopherol or its esters, superoxide dismutases, certain metal-chelating agents or ascorbic acid and its esters; (k) antiseborthoeic agents such as progesterone; (l) antidandruffagents such as octopirox or zinc pyrithione; (m) antiacne agents such as retinoic acid or benzoyl peroxide.

In some embodiments, the second agent is gabapentin, pregabalin, menthol, boswellic acid, DMSO, methyl sulfonylmethan, emu oil, hyaluronic acid, santalol, santalyl acetate, amyris alcohol, amyris acetate, or combinations thereof. U.S. Patent Publication No. 20140134261.

In certain embodiments, combination therapy means simultaneous administration of the compounds in the same composition, simultaneous administration of the compounds in separate compositions, or separate administration of the compounds (in separate compositions).

In certain embodiments, the second agent/treatment is used as adjunctive therapy to the present compound or composition. In certain embodiments, the treatment includes a phase wherein treatment with the second agent/treatment takes place after treatment with the present compound or composition has ceased. In certain embodiments, the treatment includes a phase where treatment with the present compound or composition and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present compound or composition and a second agent. In certain embodiments, a subject is treated initially with the present compound or composition, followed by cessation of the present compound or composition treatment and initiation of treatment with a second agent. In certain embodiments, the present compound or composition is used as an initial treatment, e.g., by administration of one, two or three doses, and a second agent is administered to prolong the effect of the present compound or composition, or alternatively, to boost the effect of the present compound or composition. A person of ordinary skill in the art will recognize that other variations of the presented schemes are possible, e.g., initiating treatment of a subject with the present compound or composition, followed by a period wherein the subject is treated with a second agent as adjunct therapy to the present compound or composition treatment, followed by cessation of the present compound or composition treatment.

The present compound and the other pharmaceutically active agent(s) may be administered together or separately and, when administered separately this may occur simultaneously or sequentially in any order. The amounts of the present compound and the other pharmaceutically active agent(s) and the relative timings of administration will be selected in order to achieve the desired combined therapeutic effect.

In various embodiments, the therapies (e.g., a composition provided herein and a second agent in a combination therapy) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, the therapies are administered no more than 24 hours apart or no more than 48 hours apart. In certain embodiments, two or more therapies are administered within the same patient visit. In other embodiments, the composition provided herein and the second agent are administered concurrently. In other embodiments, the composition provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a composition provided herein and a second agent are administered to a subject in a sequence and within a time interval such that the composition provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the composition provided herein and the second active agent exerts their effect at times which overlap. Each second active agent can be administered separately, in any appropriate form and by any suitable route. In other embodiments, the composition provided herein is administered before, concurrently or after administration of the second active agent. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the present agent/compound. In one embodiment, the composition provided herein is administered concurrently with one or more second agents in the same pharmaceutical composition. In another embodiment, a composition provided herein is administered concurrently with one or more second agents in separate pharmaceutical compositions. In still another embodiment, a composition provided herein is administered prior to or subsequent to administration of a second agent. Also contemplated are administration of a composition provided herein and a second agent by the same or different routes of administration, e.g., oral and parenteral. In certain embodiments, when the composition provided herein is administered concurrently with a second agent that potentially produces adverse side effects including, but not limited to, toxicity, the second active agent can advantageously be administered at a dose that falls below the threshold that the adverse side effect is elicited.

Encompassed by the present disclosure are methods to prophylactically treat a subject prior to erythema (e.g., rebound erythema). In certain embodiments, the present method prevents or delays rebound erythema in a subject.
Dosages The present agent (such as a capsaicinoid including capsaicin or a derivative, analogue, or salt thereof, and other compounds as described herein) may be present in the present composition in an amount ranging from about 0.001 wt % to about 5 wt %, from about 0.001 wt % to about 2 wt %, from about 0.001 wt % to about 1.5 wt %, from about 0.001 wt % to about 1 wt %, from about 0.001 wt % to about 0.8 wt %, from about 0.001 wt % to about 0.5 wt %, from about 0.002 wt % to about 0.3 wt %, from about 0.005 wt % to about 0.2 wt %, from about 0.005 wt % to about 0.1 wt %, from about 0.005 wt % to about 0.08 wt %, from about 0.005 wt % to about 0.05 wt %, from about 0.005 wt % to about 0.04 wt %, from about 0.005 wt % to about 0.03 wt %, from about 0.005 wt % to about 0.02 wt %, from about 0.01 wt % to about 0.08 wt %, from about 0.01 wt % to about 0.075 wt %, from about 0.01 wt % to about 0.06 wt %, from about 0.025 wt % to about 0.08 wt %, from about 0.025 wt % to about 0.075 wt %, from about 0.01 wt % to about 0.05 wt %, from about 0.01 wt % to about 0.04 wt %, from about 0.01 wt % to about 0.03 wt %, from about 0.01 wt % to about 0.02 wt %, from about 0.01 wt % to about 0.025 wt %, about 0.005 wt %, about 0.006 wt %, about 0.007 wt %, about 0.008 wt %, about 0.009 wt %, about 0.01 wt %, about 0.011 wt %, about 0.012 wt %, about 0.013 wt %, about 0.014 wt %, about 0.015 wt %, about 0.016 wt %, about 0.017 wt %, about 0.018 wt %, about 0.019 wt %, about 0.02 wt %, or about 0.025 wt %, of the total weight of the composition. The present agent (such as a capsaicinoid including capsaicin or a derivative, analogue, or salt thereof, and other compounds as described herein) may be present in the present composition in an amount ranging from 0.20-30% by weight, 0.075-30% by weight, 0.2-30%, or 2-20%, 2-10%, 5-15%, 0.075-30 wt. %, 0.2 wt % to 30 wt %, between 1 wt % and 20 wt %, e.g. 1 wt %, 5 wt %, 10 wt %, and 20 wt %, from about 10% to about 50% by weight, from about 10% to about 40% by weight, from about 10% to about 30% by weight, from about 10 to about 25% by weight, from about 10% to about 20% by weight, or from about 10% to about 15% by weight, of the total weight of the composition.

When a capsaicinoid other than capsaicin is used in the present composition, since potency can vary, the amount of the capsaicinoid in the composition may be the amount which achieves the same or similar results achieved by the weight percent ranges for capsaicin. In one embodiment, the dose of resiniferatoxin is 10-fold less, 20-fold less, 30-fold less, 40-fold less, 50-fold less, 60-fold less, 70-fold less, 80-fold less, 100-fold less, at least 100-fold less, 120-fold less, 150-fold less, or 200-fold less, than a dose of capsaicin.

A substance P antagonist may be present in the present composition in an amount ranging from about 0.000001 wt % to about 10 wt %, from about 0.0001 wt % to about 5 wt %, from about 0.001 wt % to about 5 wt %, from about 0.01 wt % to about 5 wt %, from about 0.1 wt % to about 5 wt %, or from about 0.5 wt % to about 5 wt %, of the total weight of the composition.

The alpha-adrenergic agonist (as described herein) may be present in the present composition in an amount ranging from about 0.01 wt % to about 2 wt %, from about 0.02 wt % to about 1.5 wt %, from about 0.03 wt % to about 1 wt %, from about 0.04 wt % to about 0.8 wt %, from about 0.05 wt % to about 0.6 wt %, from about 0.06 wt % to about 0.5 wt %, from about 0.07 wt % to about 0.4 wt %, from about 0.08 wt % to about 0.3 wt %, from about 0.06 wt % to about 0.3 wt %, from about 0.09 wt % to about 0.3 wt %, from about 0.1 wt % to about 0.25 wt %, from about 0.1 wt % to about 0.2 wt %, from about 0.1 wt % to about 0.15 wt %, from about 0.05 wt % to about 0.25 wt %, from about 0.05 wt % to about 0.2 wt %, from about 0.05 wt % to about 0.15 wt %, from about 0.1 wt % to about 0.3 wt %, from about 0.05 wt % to about 0.3 wt %, about 0.05 wt %, about 0.06 wt %, about 0.07 wt %, about 0.08 wt %, about 0.09 wt %, about 0.1 wt %, about 0.11 wt %, about 0.12 wt %, about 0.13 wt %, about 0.14 wt %, about 0.15 wt %, about 0.16 wt %, about 0.17 wt %, about 0.18 wt %, about 0.19 wt %, about 0.2 wt %, about 0.25 wt %, about 0.3 wt %, about 0.4 wt %, about 0.5 wt %, about 0.6 wt %, about 0.7 wt %, or about 0.8 wt %, of the total weight of the composition.

As used herein, "wt %", "% w/w" or "% (w/w)" refer to % by weight of the composition.

In certain embodiments, the amount of a topical formulation applied to the affected skin area ranges from about 0.01 $g/cm^2$ of skin surface area to about 5 $g/cm^2$, from 0.2 $g/cm^2$ to about 0.5 $g/cm^2$, from about 0.0001 $g/cm^2$ to about 0.05 $g/cm^2$, from about 0.0001 $g/cm^2$ to about 0.01 $g/cm^2$, from about 0.001 $g/cm^2$ to about 0.003 $g/cm^2$, or from 0.002 $g/cm^2$ to about 0.005 $g/cm^2$ of skin surface area.

The present composition may be administered once, twice, three times, four times, five times, six times or more per day, or as needed, during the course of treatment. In certain embodiments, the present agent/composition is administered at least once a day, at least twice a day, at least three times per day, or more. In certain embodiments, the present agent/composition is administered at least once a week, at least twice a week, at least three times a week, at least once per month, at least twice per month, or more frequently. Treatment can continue as long as needed. In one embodiment, the topical composition is topically applied to the affected skin area once daily.

The present composition may be administered daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the present composition. In certain embodiments, a single dose of the present agent/composition is administered in the present method. In certain embodiments, multiple doses of the present agent/composition (e.g., 2 doses, 3 doses, 4 doses, 5 doses, 6 doses, 7 doses, 8 doses, 9 doses, 10 doses or more) are administered in the present method.

In certain embodiments, the administration of the present agent/composition is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present agent/composition is administered once, twice, at least twice, at least three times, at least four times, at least five time, at least six times, at least seven times, at least eight times, at least nine times, or more per treatment.

Subjects

The subject may be a human. In an embodiment, the subject is or will be treated with a treatment that may cause erythema, or is prone to erythema. In still another embodiment, the subject is suffering from erythema and is or will be treated with a treatment that may treat erythema and/or ameliorate the appearance of erythema. In an embodiment, the subject is suffering from a skin disease, which may be selected from the group consisting of rosacea, psoriasis, atopic eczema or atopic dermatitis (neurodermatitis), eczema, or acne. In an embodiment, the subject is suffering from a disease affecting internal or external mucosa, e.g. oral, nasal, or intestinal mucosa. For example, the subject is suffering from inflammatory bowel disease, Morbus Crohn (or Crohn's disease), aphthous stomatitis, conjunctivitis, chronic obstructive pulmonary disease, peptic ulcers, alcohol abuse, or gastritis. In an embodiment, the subject is suffering from a somatoform disorder, such as blushing.

In certain embodiments, the subject is a non-human animal. The non-human animal may be a mammal selected from the group consisting of primates (non-human primates), pigs, rodents, or rabbits. In an embodiment, the subject is a pig, such as a miniswine. In another embodiment, the subject is a mouse.

Kits

The present disclosure also encompasses an article of manufacture, e.g., a kit. The article of manufacture may contain the present composition in a suitable container with labeling and instructions for use. In certain embodiments, the container can be a dropper or tube with a suitable small orifice size, such as an extended tip tube made of any pharmaceutically suitable material. The topical formulations can be filled and packaged into a plastic squeeze bottle or tube. Optionally, an applicator can be provided in or attached to the container, or separately from the container.

Instructions may be packaged with the composition, for example, a pamphlet or package label. The labeling instructions explain how to the present composition, in an amount and for a period of time sufficient to treat or prevent erythema and its symptoms. In certain embodiments, the label includes the dosage and administration instructions, the topical formulation's composition, the clinical pharmacology, drug resistance, pharmacokinetics, absorption, bioavailability, and/or contraindications.

Topical Administration

In certain embodiments, the present composition is formulated for topical administration. The terms "topically administrable composition," a "topical composition," or a "topical formulation," as used herein, refer to any formulation or composition which is pharmaceutically and/or cosmetically acceptable for topical delivery of the specified compounds according to embodiments of the invention. The composition may be administered to a defined area of the body such as a defined area of skin surface or mucous membrane.

The present composition may additional contain a physiologically acceptable medium, such as a vehicle and/or a carrier. By "physiologically acceptable medium" is intended a cosmetically and/or dermatologically acceptable medium, which is compatible with the skin.

In some embodiments, the present composition can additionally include one or more pharmaceutically acceptable excipients. One of ordinary skill in the art would be familiar with pharmaceutically acceptable excipients. For example, the pharmaceutically acceptable excipient may be a water soluble sugar, such as mannitol, sorbitol, fructose, glucose, lactose, and sucrose.

The present composition can be formulated in any pharmaceutical form normally provided for topical application to the skin, in particular formulated as solutions or dispersions of lotion or serum type, emulsions of liquid or semi-liquid consistency of the milk type, obtained by dispersion of a fatty phase in an aqueous phase (O/W) or, conversely, (W/O), or suspensions or emulsions of soft consistency of the aqueous or anhydrous cream or gel type, or, alternatively, microgranules, nanoparticles, microemulsions, nanocapsules, or vesicle dispersions of ionic and/or nonionic type.

Exemplary forms of formulation that can be used for topical administration include, but are not limited to, sprays, mists, aerosols, solutions, lotions, gels, serum, creams, ointments, pastes, unguents, emulsions and suspensions. The composition may be in the form of aqueous, aqueous/alcoholic or oily solutions, dispersions of lotion or serum type, aqueous anhydrous or lipophilic gels, emulsions of liquid or semi-liquid consistency of the milk type, obtained by dispersion of a fatty phase in an aqueous phase or conversely an aqueous phase in a fatty phase, or suspensions or emulsions of semi-solid or solid consistency of the cream or gel type, soaps or detergents, or alternatively microemulsions, microcapsules, microparticles, or vesicle dispersions of ionic and/or non-ionic type. Among additional alternative means for topical application of the compositions are spray pumps, aerosol dispersions, impregnated cosmetic facial masks, and impregnated cosmetic facial cloths or sponges.

The composition may be a cleansing, protective, treatment or care cream for the face, for the hands, for the feet, for the major anatomical folds or for the body (for example day creams, night creams, makeup-removing creams, foundation creams, sunscreen creams, fluid foundations, makeup-removing milks, protective or care body milks, antisun (sunscreen) milks, skincare lotions, gels or mousses, as cleansing lotions, sunscreen lotions, artificial tanning lotions, bath compositions, deodorizing compositions containing a bactericidal agent, aftershave lotions or gels, hair-removing creams, compositions to combat insect bites and analgesic compositions. The composition can also be formulated as a solid preparation constituting a cleansing bar or a soap. The composition can be formulated as a shampoo or a conditioner, or a toothpaste.

To treat or prevent erythema or a symptom associated therewith, the present composition may be topically applied directly to the affected area in any conventional manner known in the art, e.g., by dropper, applicator stick, or cotton swab, as a mist via an aerosol applicator, via an intradermal or transdermal patch, or by simply spreading a formulation of the invention onto the affected area with fingers, a sponge, a pad, or wipes. The composition of the present invention can be used topically by rubbing over an area to be treated. A typical method of use is to rub the formulation over the entire area, until the formulation disappears. For liquids formulations, dispensers can include tubes and/or bottles with a sponge or a roll-on applicator such as roller bottles. U.S. Patent Publication No. 20160106690. Additionally, the amount of formulation used can be gradually increased with each successive application.

In certain embodiments, the topically composition are prepared by mixing a pharmaceutically acceptable carrier with the present agent according to known methods in the art, for example, methods provided by standard reference texts such as, Remington: The Science and Practice of Pharmacy 1577-1591, 1672-1673, 866-885 (Alfonso R. Gennaro ed. 19th ed. 1995); Ghosh, T. K.; et al. Transdermal and Topical Drug Delivery Systems (1997), both of which are hereby incorporated herein by reference.

The present composition may contain a gelling agent, a polyol, a protective agent, a cosmetic agent, an adsorbent, a preservative, an antioxidant, a surfactant, a skin-penetration agent, a local anesthetic, an analgesic etc.

Suitable gelling agents known in the art, including those used in the two-phase or single-phase gel systems, can be used in the present invention. Some examples of suitable gelling agents are disclosed in Remington: The Science and Practice of Pharmacy 1517-1518 (Alfonso R. Gennaro ed. 19th ed. 1995), which is hereby incorporated herein by reference. The gelling agents include, but are not limited to, one or more hydrophilic and hydroalcoholic gelling agents used in the cosmetic and pharmaceutical industries. Non-limiting examples of gelling agents include hydroxyethylcellulose, cellulose gum, MVE/MA decadiene crosspolymer, PVM/MA copolymer, glycerine polyacrylate, or a combination thereof. Exemplary hydrophilic gelling agents include carboxyvinyl polymers (carbomer), acrylic copolymers such as acrylate/alkylacrylate copolymers, polyacrylamides, polysaccharides such as hydroxypropylcellulose, natural gums and clays, and, exemplary lipophilic gelling agents include modified clays such as bentones, metal salts of fatty acids such as aluminum stearates, and hydrophobic silica. Exemplary hydrophilic active agents are proteins or protein hydrolysates, amino acids, polyols, urea, allantoin, sugars and sugar derivatives, vitamins and hydroxy acids.

Polyols in gel formulations can serve one or more functions such as solubilizing agents, moisturizers, emollients, skin humectant, skin-penetration agents, etc. Suitable polyols that can be used in embodiments of the present invention include, but are not limited to, glycerine, propylene glycol, dipropylene glycol, hexylene glycol, butylene glycol, and liquid polyethylene glycols, such as polyethylene glycol 200 to 600. Ofher et al., Gels and Jellies, pp. 1327-1344 of Encyclopedia of Pharmaceutical Technology, vol. 3 (ed. by Swarbrick, et al, pub. by Marcel Dekker, 2002); or Pena, "Gel Dosage Forms: Theory, Formulation, and Processing," pp. 381-388 of Topical Drug Delivery Formulations, (ed. by Osborne et al., pub. by Marcel Dekker, Inc., 1990).

Suitable preservatives include, but are not limited to, quaternary ammonium compounds, such as benzalkonium chloride, benzethonium chloride, cetrimide, dequalinium chloride, and cetylpyridinium chloride; alcoholic agents, for example, chlorobutanol, phenylethyl alcohol, and benzyl alcohol; parabens such as methylparaben, ethylparaben, propylparaben, and butylparaben; antibacterial esters, for example, esters of parahydroxybenzoic acid; and other antimicrobial agents such as chlorhexidine, chlorocresol, benzoic acid, polymyxin, and phenoxyethanol. Preferably, the preservative is selected from the group consisting of sodium benzoate, phenoxyethanol, benzyl alcohol, methylparaben, imidazolidinyl urea and diazolidinyl urea.

Topical administration can continue for about 1 day, about 2 days, about 3 days, about 4 days, about 5 days, about 6 days, about 7 days, about 2 weeks, about 3 weeks, about 4 weeks, about 2 months, about 3 months, about 4 months, about 5 months, about 6 months, about 1 year or longer.

In some embodiments, the present composition may comprise one or more pharmaceutically acceptable antioxidants. Any pharmaceutically acceptable antioxidant known to those of ordinary skill in the art is contemplated for inclusion in the present pharmaceutical compositions. For example, the pharmaceutically acceptable antioxidant may be selected from the group consisting of ascorbic acid, sodium ascorbate, sodium bisulfate, sodium metabisulfite and monothio glycerol.

In some embodiments, the present composition may comprise one or more pharmaceutically acceptable buffering agents. Any pharmaceutically acceptable buffering agent known to those of ordinary skill in the art is contemplated for inclusion in the present pharmaceutical compositions. Examples of such buffering agents include of monobasic sodium phosphate, dibasic sodium phosphate, sodium benzoate, potassium benzoate, sodium citrate, sodium acetate, and sodium tartrate.

The pH of the topical formulations may be within a physiologically acceptable pH, e.g., within the range of about 4 to about 8, of about 6 to about 7.5, or about 4.5 to 6.5.

In some embodiments, the present composition may or may not comprise one or more pharmaceutically acceptable skin penetration enhancers. Examples of such skin penetration enhancers include but not limited to fatty alcohols such as decanol, lauryl alcohol, linolenyl alcohol, n-octanol and oleyl alcohol; fatty acid esters such as ethyl acetate, dodecyl N,N-dimethylamino acetate, glycerol monolaurate, glycerol monooleate, isopropyl myristate, methyl laurate and sorbitan monooleate; fatty acids such as lauric acid and oleic acid; biologics such as lecithin, amines and amides such as N,N-dimethyl-m-toluamide, lauryl-amine and urea; complexing agents such as cyclodextrin, hydroxypropyl methylcellulose and liposomes; surfactants such as Brij 36T, sodium lauryl sulfate and sorbitan monooleate; other compounds such as dimethyl isosorbide, bisabolol, eucalyptol, menthol, terpenes, N-methyl pyrrolidone, azone, DMSO, MSM, decylmethyl sulfoxide, dimethyl formamide, dimethyl acetamide, glycols and propylene glycol.

Exemplary oils that may be used in the present composition, include mineral oils (liquid petroleum jelly), plant oils (liquid fraction of karite butter, sunflower oil), animal oils (perhydrosqualene), synthetic oils (purcellin oil), silicone oils (cyclomethicone) and fluoro oils (perfluoropolyethers). Fatty alcohols and fatty acids (stearic acid) can be added to these oils.

Exemplary emulsifiers that may be used in the present composition, include glyceryl stearate, polysorbate 60 and the mixture PEG-6/PEG-32/glycol stearate.

Representative solvents which can be used include the lower alcohols, such as ethanol and isopropanol.

In certain other embodiments, a surfactant can be used in the present composition, as a wetting agent, emulsifier, solubilizer and/or antimicrobial.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof.

In some embodiments, the topical formulations may contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Administration Routes

The present composition may be administered topically, orally, via implant, parenterally, sublingually, rectally, topically, via infiltration, or via inhalation. Injection or implantation includes, but is not limited to subcutaneous (under the skin), intramuscular (muscle), itrathecal, epidural, intraperitoneal, caudal, intradermal or intracutaneous (into the skin), intercostals at a single nerve, intra-articular (joints) or body spaces, intrasynovial (joint fluid), intraspinal (spinal column), intra-arterial (arteries) administrations and administration into body spaces include pleura, peritoneium, cranium, mediastinum, pericardium, and bursae or bursal. The present composition may be administered intra-articularly, intra-sternally, intrasynovially, intra-bursally or into body spaces.

This invention will be better understood from the following examples. However, one skilled in the art will readily appreciate that the specific methods and results discussed are merely illustrative and not limiting.

In the example to follow, all parts and percentages are given by weight.

EXAMPLE 1

Effect of Topical Capsaicin on Persistent Patchy and Transient Diffuse Cutaneous Erythema Associated with the Use of Topical Alpha Adrenergic Agonists The topical alpha-2 adrenergic agonist, brimonidine tartrate gel is currently approved to treat facial erythema and flushing in patients with rosacea. Common side effects of repeated brimonidine gel use are early transient superficial flushing and persistent, patchy erythema. This study reports the efficacy of topical capsaicin combined with topical brimonidine in treating these side effects. Reformulating the currently approved brimonidine tartrate gel to include a capsaicinoid can improve patient tolerance and decrease side effects.

Methods

All experiments were conducted on a single patient with a long-standing diagnosis of erythrotelangiectatic acne rosacea. The treated areas of the left, right and full face were photographed at various time points before and after drug applications.

Varying concentrations of brimonidine gel with or without capsaicin were compounded using commercially available 0.5 wt % brimonidine tartrate gel (Mirvaso®) and OTC (over-the-counter) 0.1 wt % capsaicin cream. The concentrated active ingredients in each were diluted to the desired concentration by combining them with a carrier vehicle such as a sandalwood oil and/or rose oil facial moisturizer. For the composition containing a combination of 0.25 wt % brimonidine and 0.25 wt % capsaicin, 2 parts of 0.5 w-% brimonidine gel was mixed with one part of 0.1 wt % capsaicin cream and one part of a carrier vehicle. The resulting combinations mixed well, were found to be homogenous and were used immediately after compounding.

The tolerability of various concentrations of capsaicin cream alone was tested by compounding OTC 0.1 wt % capsaicin cream with a carrier vehicle. These combinations were applied to the subject's face. The sense and degree of irritation, pain, and/or burning were noted. Photos to document the degree of flushing of the treated skin were taken.

A 3-day trial of bilaterally applied 0.20-0.25 wt % brimonidine gel alone was performed. 0.20-0.25 wt % brimonidine gel combined with a carrier vehicle was applied to the entire face once daily. Notes were taken and the results were photographically documented at several time points over the course of the trial.

The effects of topical 0.20-0.25 wt % brimonidine gel/0.020-0.025 wt % capsaicin cream, and topical 0.10-0.15 wt % brimonidine gel/0.010 wt % capsaicin cream, applied bilaterally to the face were also assessed and compared in two separate trials.

The first trial consisted of 4 days of treatment with 0.20-25 wt % brimonidine gel/0.020-0.025 wt % capsaicin cream followed by 4 days of observation. The second trial consisted of two separate single day bilateral treatments with 0.10-0.15 wt % brimonidine gel/0.010 wt % capsaicin cream followed by 1 day of observation. Notes were taken and the results were photographically documented at several time points over the course of the trials.

Results

In summary, brimonidine tartrate gel (0.20-0.25 wt %) used alone resulted in the development of patchy cutaneous erythema that persisted and worsened with continued use. Combining capsaicin (0.020-0.025 wt %) with brimonidine gel (0.20-0.25 wt %) inhibited the development of persistent patchy facial erythema while still retaining the clinical effectiveness profile of topical brimonidine gel alone.

A lower concentration combination of 0.10-0.15 wt % brimonidine gel combined with 0.01 wt % capsaicin had similar efficacy at treating erythema/preventing rebound erythema, and produced less burning sensation upon application. Although early, mild superficial flushing periodically occurred, this could be quickly ameliorated by reapplication of the 0.10-0.15 wt % brimonidine/0.010 wt %, capsaicin combination, or by reapplication of 0.010 wt % capsaicin alone. No persistent patchy erythema was observed at any time when capsaicin was present. The detailed experimental results are as follows.

Capsaicin Cream Alone

Figures 2A, 2B, 2C:
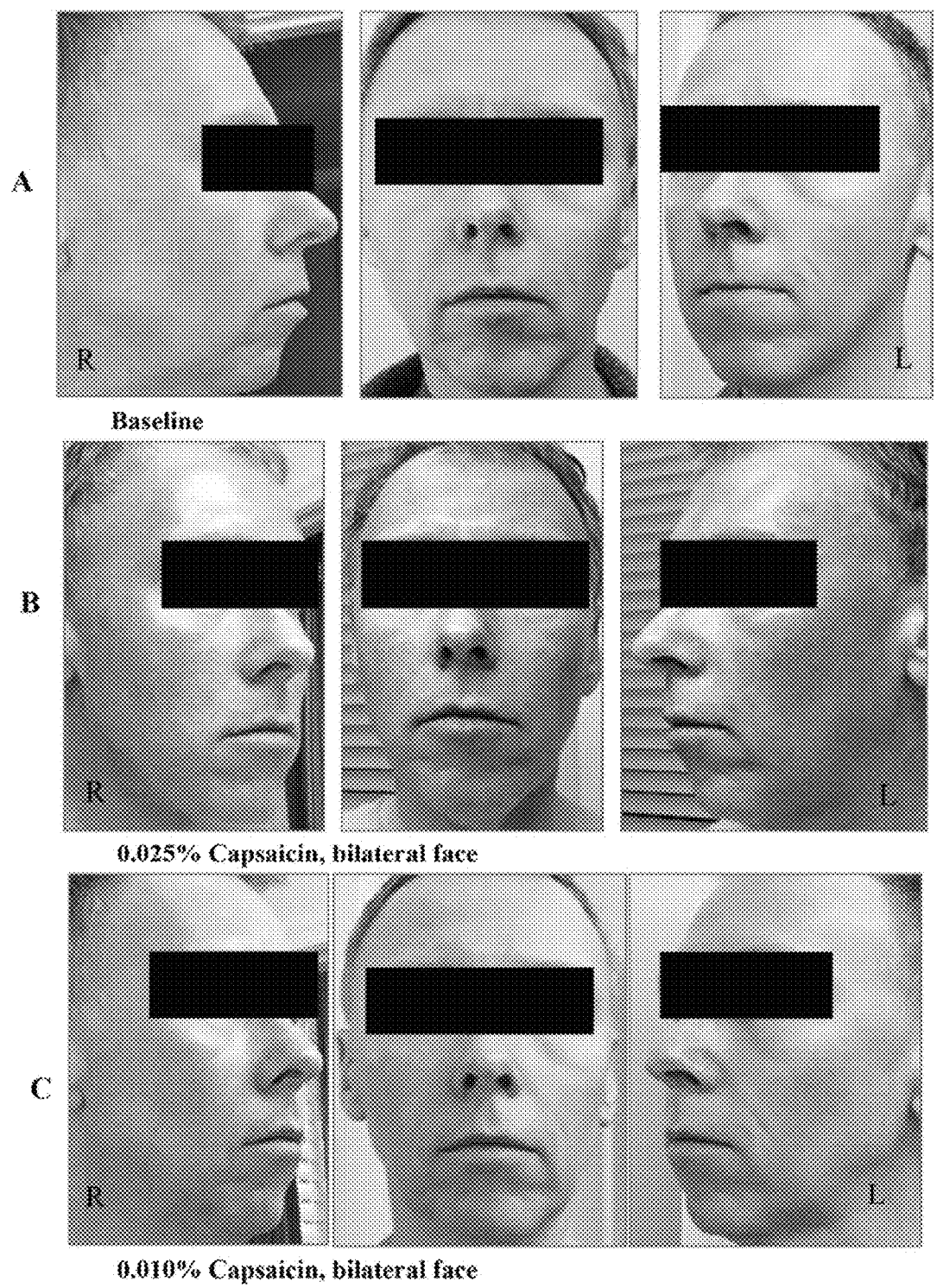
FIGS. 2A-2C: Facial erythema/flushing following application of varying concentrations of capsaicin cream alone.
Figures 3A, 3B, 3C:
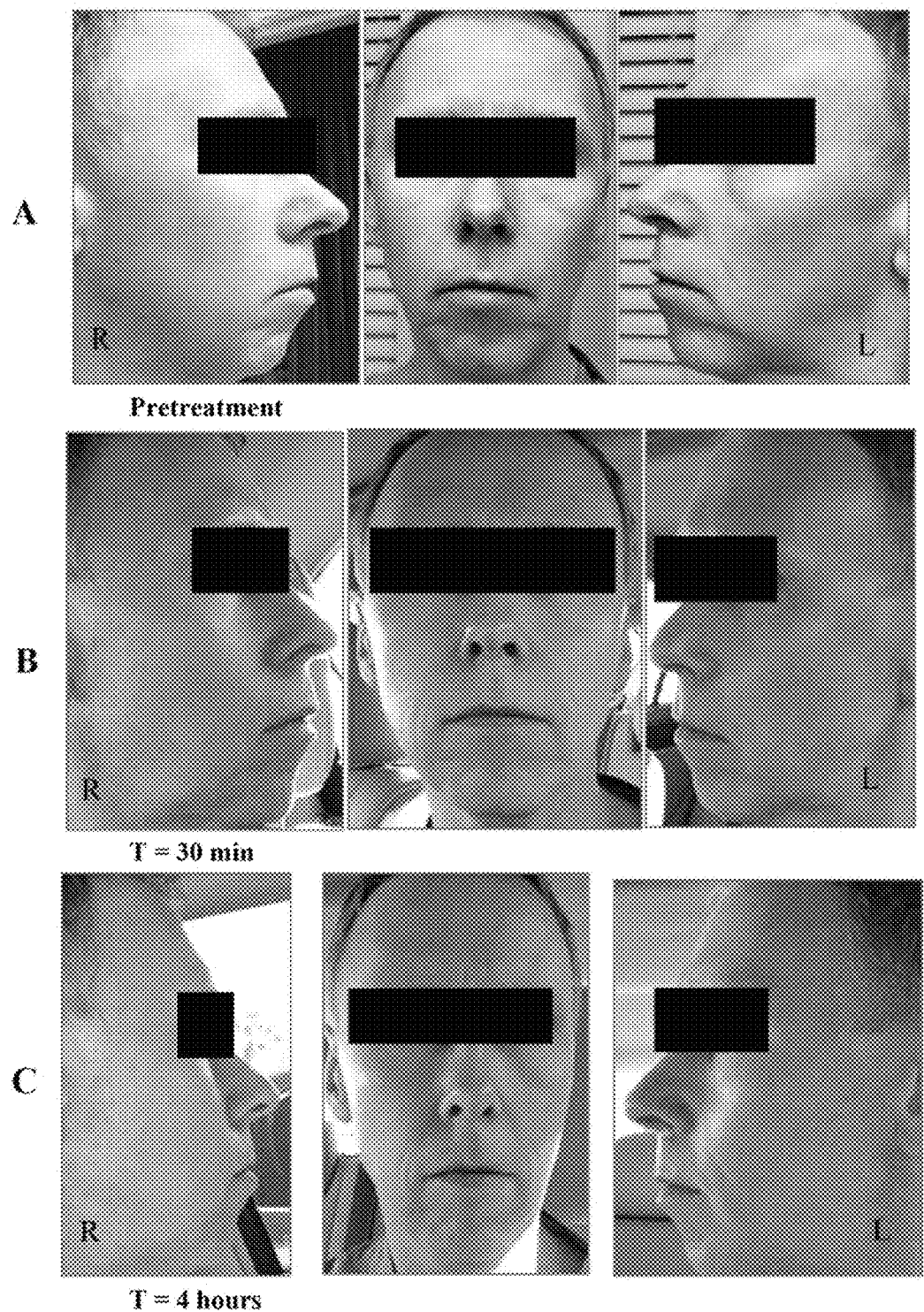
FIGS. 3A-3F: Representative photos of 3-day trial in which 0.20-0.25% brimonidine gel in vehicle was applied. Brimonidine gel was clinically effective at reducing erythema associated with rosacea. T=0 (pretreatment, FIG. 3A), T=30 min (FIG. 3B), T=4 hours (FIG. 3C), T=6 hours (FIG. 3D), T=8 hours (FIG. 3E), and T=12 hours (FIG. 3F).
Figures 3D, 3E, 3F:
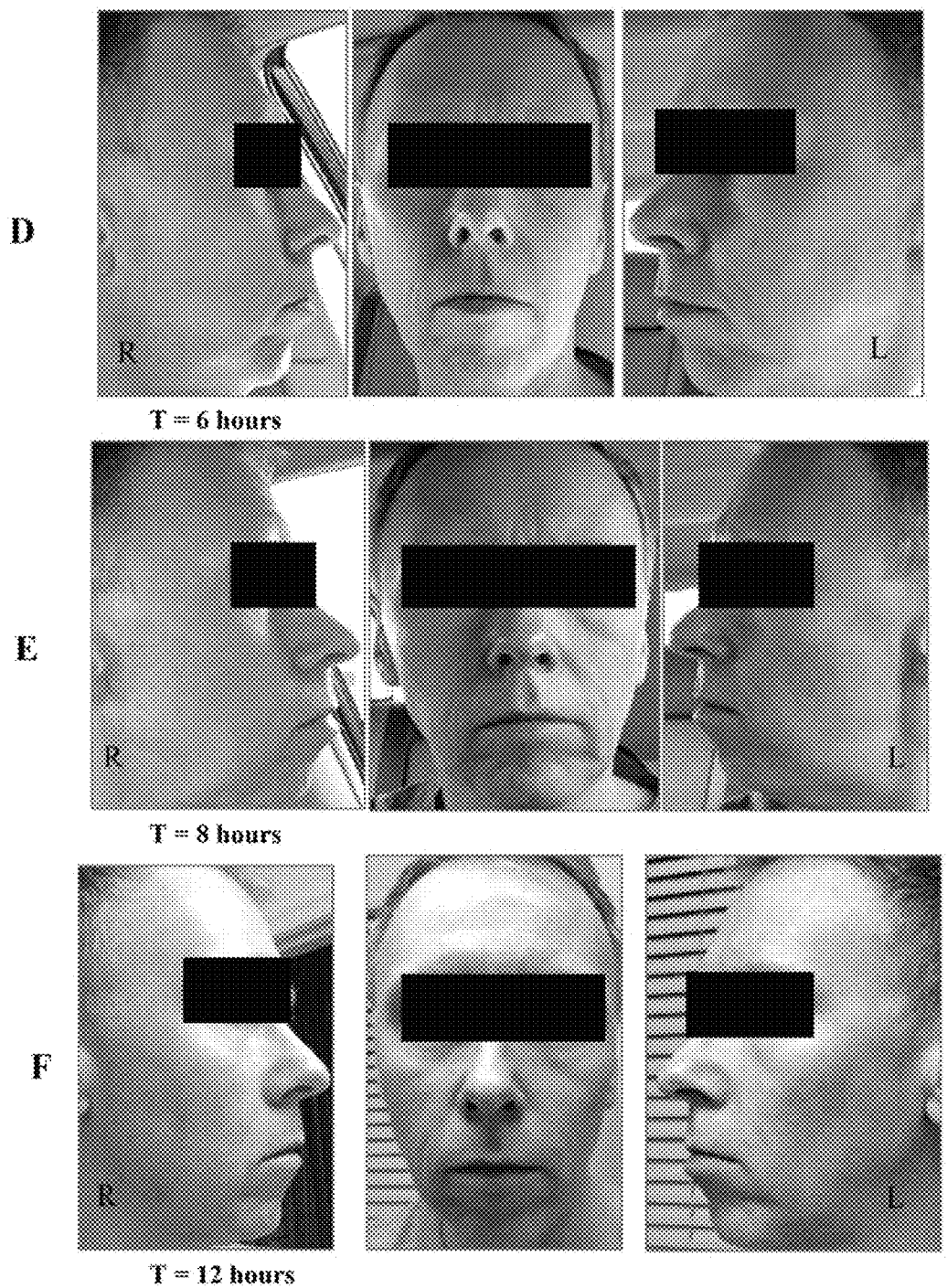

In order to determine the effects and tolerability of capsaicin on facial skin, varying concentrations of capsaicin were applied and evaluated (FIGS. 2A-2C).

0.1 wt % capsaicin: 0.1 wt % capsaicin produced extreme burning and pain, bright erythema and flushing that lasted for over 10 hours.

0.025 wt % and 0.02 wt % capsaicin: 0.025 wt % and 0.02 wt % capsaicin also produced burning that persisted for approximately 30 minutes (FIG. 2B). Facial redness was apparent for several hours and mild erythema was detectable even 8 to 10 hours after application.

0.01 wt % capsaicin: Decreasing the capsaicin concentration to 0.01 wt % produced a sensation of warmth without pain or burning that resolved within 5 to 10 minutes (FIG. 2C). With application of 0.01% capsaicin, very mild flushing developed that resolved completely in approximately 30 minutes.

Table 2 shows the CEA grading after topical application of the capsaicin formulations alone.

TABLE 2

CEA grading after administration of capsaicin formulation

| Formulations | CEA Score | Observations |
| --- | --- | --- |
| Baseline (FIG. 2A) | 1 | Mild baseline erythema. Skin is almost clear with only slight redness. |
| 0.025% Capsaicin (FIG. 2B) | 4 | Severe, rapidly-developing erythema within 5 to 10 minutes of application of 0.025% capsaicin alone. |
| 0.01% Capsaicin (FIG. 2C) | 2 | Moderate, rapidly-developing erythema within 10 minutes of application of 0.010% capsaicin alone |

0.20-0.25 wt % Brimonidine Gel in Vehicle

To establish a baseline response to brimonidine gel alone, a 3-day trial of 0.20-0.25 wt % brimonidine gel combined with vehicle was performed. Brimonidine gel (0.20-0.25 wt %) was applied once daily in the morning and results were photographed at various time points as shown in FIGS. 3A-3E. Each evening, the subject's face was treated with vehicle. As per previous studies, brimonidine was found to be clinically effective for 6-12 hours; however, patchy erythematous changes developed within 24 hours of applying the first dose and worsened throughout the trial as shown in FIG. 4. This patchy erythema was particularly noticeable each morning after application (i.e., T=24 hr). The erythema was noted to start in the buccal regions, but expanded to include the forehead and temporal areas by the end of the trial period. The erythema persisted for 48-72 hours after the final application of brimonidine/vehicle. A summary of the trial results is presented below. Table 3 shows the CEA grading after topical application of the brimonidine formulations alone.

TABLE 3

CEA grading after administration of brimonidine formulation

| Formulations Time after administration | CEA Score | Observations |
| --- | --- | --- |
| Baseline (FIG. 3A) | 2 | Mild baseline erythema with definite redness |
| 0.20-0.25% brimonidine, 30 min (FIG. 3B) | 1 | Gradual and marked decrease in erythema noted by t = 20 min. Skin is almost clear with only slight redness. Stable at t = 30 min (photo) |
| 0.20-0.25% brimonidine, 4 hours (FIG. 3C) | 0 | Gradual and complete resolution of erythema achieved by t = 1 hr. Clear skin with no signs of erythema. Persisted CEA = 0 until photo at t = 4 hr. |
| 0.20-0.25% brimonidine, 6 hours (FIG. 3D) | 1 | Mild and gradual increase in erythema between t = 4 hr and t = 8 hr. Skin is almost clear with only slight redness. |
| 0.20-0.25% brimonidine, 8 hours (FIG. 3E) | 2 | Gradual increase in erythema between t = 8 hr and t = 12 hr. |
| 0.20-0.25% brimonidine, 12 hours (FIG. 3F) | 3 | Erythema at moderate baseline level at t = 12 hr. |

Treatment Day 1:
Pretreatment: Typical baseline erythema secondary to rosacea is present. Left and right side of face appear similar.
T=0-approximately 9 hr: Brimonidine gel clinically effective.
T=12-24 hr: Development of patchy/blotchy erythema bilaterally. Appears more pronounced than pretreatment erythema.
Treatment Day 2:
Pretreatment: Increased patchy erythema noted.
T=0-6 hr: Erythema resolved.
T=8 hr: superficial flushing noted.
T=13-24 hr: Patchy erythema noted.
Treatment Day 3:
Pretreatment: Increased patchy erythema noted.
T=0-5 hr: Erythema resolved.
T=8-24 hr: Patchy erythema appears worsened.

In summary, treatment with 0.20-0.25% brimonidine gel alone resulted in the appearance of patchy erythema within the first 24 hours after application (FIG. 4). The erythema persisted and worsened throughout the trial.

0.20-0.25% Brimonidine Gel/0.020-0.025% Capsaicin Cream

In order to determine whether addition of topical capsaicin cream to brimonidine gel affects development of facial erythema post alpha agonist use, a 4-day trial was conducted wherein the test subject's face was treated with 0.20-0.25 wt/brimonidine gel/0.020-0.025 wt % capsaicin combination. Additionally, at the end of each treatment day, the test subject's face was treated with 0.025 wt % capsaicin in vehicle. Four days of observation wherein no treatment was given, followed the trial. Representative photos of treatment and observation are shown in FIG. 5. At no time did persistent, patchy erythematous changes develop. A summary of the trial results is presented below. Table 4 shows the CEA grading after topical application of the 0.20-0.25 wt % brimonidine/0.020-0.025 capsaicin formulations.

TABLE 4

CEA grading after administration of 0.20-0.25 wt % brimonidine/0.020-0.025 wt % capsaicin formulation

| Formulations, Time after administration | CEA Score | Observations |
| --- | --- | --- |
| Baseline (FIG. 5A) | 2 | Mild baseline erythema with definite redness |
| 0.20-0.25% brimonidine/0.020-0.025% capsaicin, 30 min (FIG. 5B) | 1 (about a 1-grade improvement within about 20 minutes or about 30 minutes as evaluated by CEA) | Gradual and marked decrease in erythema and redness noted by t = 20 min. Skin is almost clear with only slight redness. Stable at t = 30 min (photo). |
| 0.20-0.25% brimonidine/0.020-0.025% capsaicin, 4 hours (FIG. 5C) | 0 (about a 2-grade improvement within about 1 hour as evaluated by CEA) | Gradual and complete resolution of erythema achieved by t = 1 hr. Clear skin with no signs of erythema. Persisted CEA = 0 until photo at t = 4 hr. |
| 0.20-0.25% brimonidine/0.020-0.025% capsaicin, 6 hours (FIG. 5D) | 1 | Gradual return of mild erythema between t = 4 hr and t = 6 hr. Skin is almost clear with only slight redness. Photo at t = 6 hr. |

TABLE 4-continued

CEA grading after administration of 0.20-0.25 wt %
brimonidine/0.020-0.025 wt % capsaicin formulation

| Formulations, Time after administration | CEA Score | Observations |
|---|---|---|
| 0.20-025% brimonidine/0.020-0.025% capsaicin, 8 hours (FIG. 5E) | 1-2 | Gradual increase in erythema and redness between t = 6 hr and t = 8 hr. |
| 0.20-0.25% brimonidine/0.020-0.025% capsaicin, 24-48 hours (FIG. 5F) | 3 | Moderate erythema with marked redness noted at t = 24 hr. |

Figures 5A, 5B, 5C:
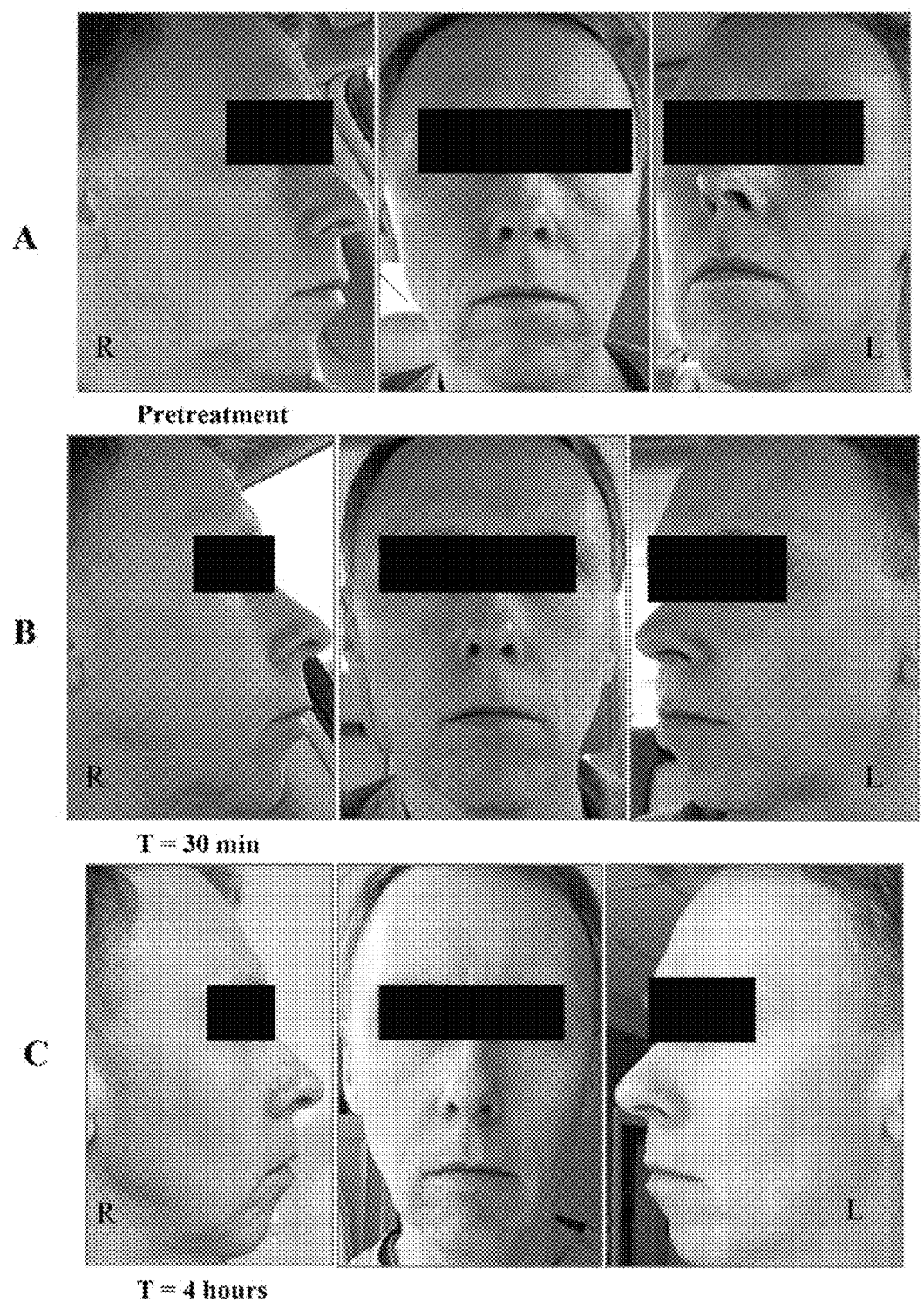
FIGS. 5A-5F: Representative photos of a 4-day bilateral trial of 0.20-0.25% brimonidine gel/0.020-0.025% capsaicin (FIGS. 5A-5E) and a 4-day observation period (FIG. 5F). Persistent patchy erythema did not develop during the trial. T=0 (pretreatment, FIG. 5A), T=30 min (FIG. 5B), T=4 hours (FIG. 5C), T=6 hours (FIG. 5D), T=8 hours (FIG. 5E), and T=24-48 hours (FIG. 5F).
Figures 5D, 5E, 5F:
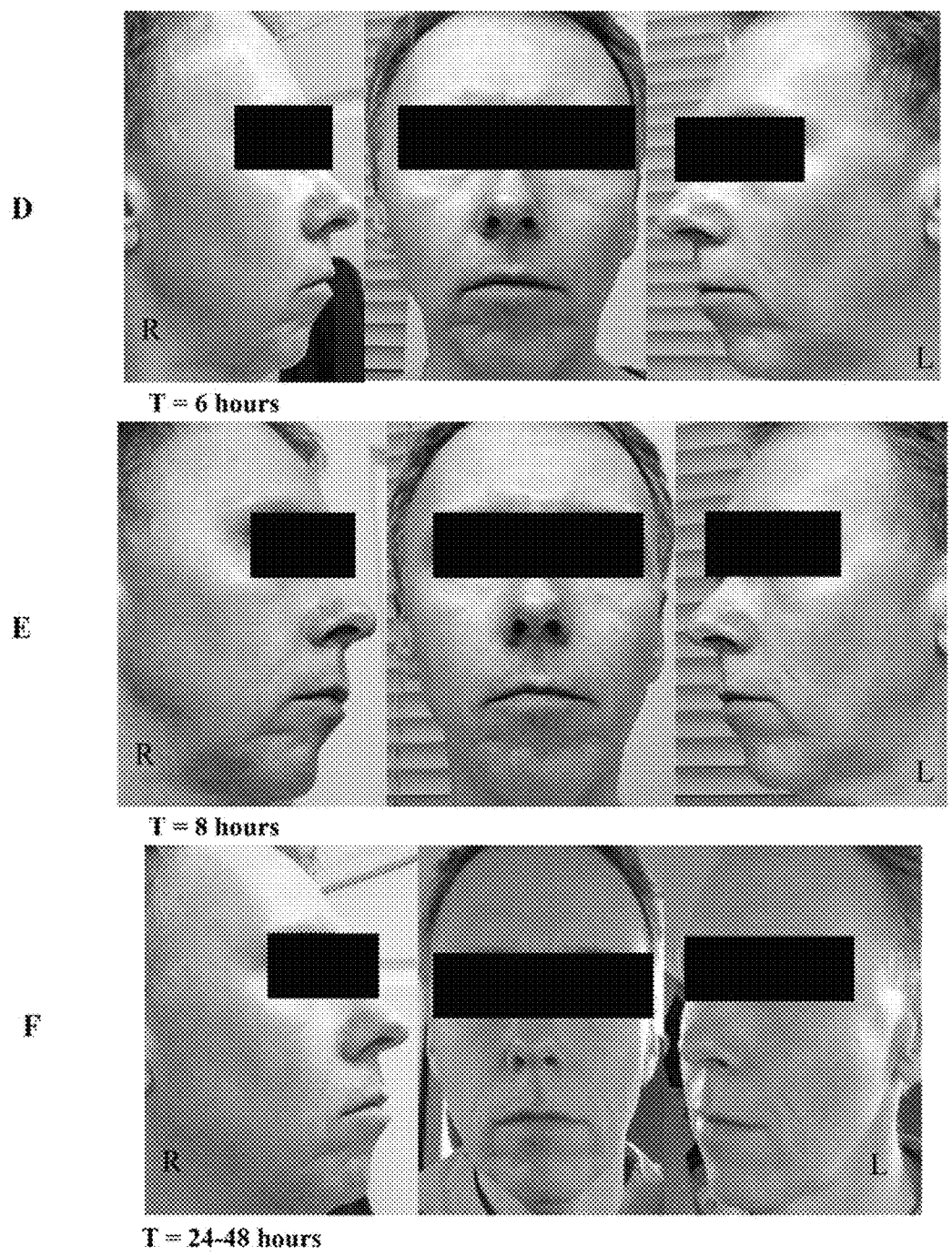
Figures 6A, 6B:
FIGS. 6A-6B: Comparison of 0.20-0.25% brimonidine gel/vehicle (FIG. 6A) versus 0.20-0.25% brimonidine gel/ 0.020-0.025% capsaicin (FIG. 6B). Addition of capsaicin to brimonidine gel prevents development of patchy erythema. R, right face.
Figures 7A, 7B, 7C:
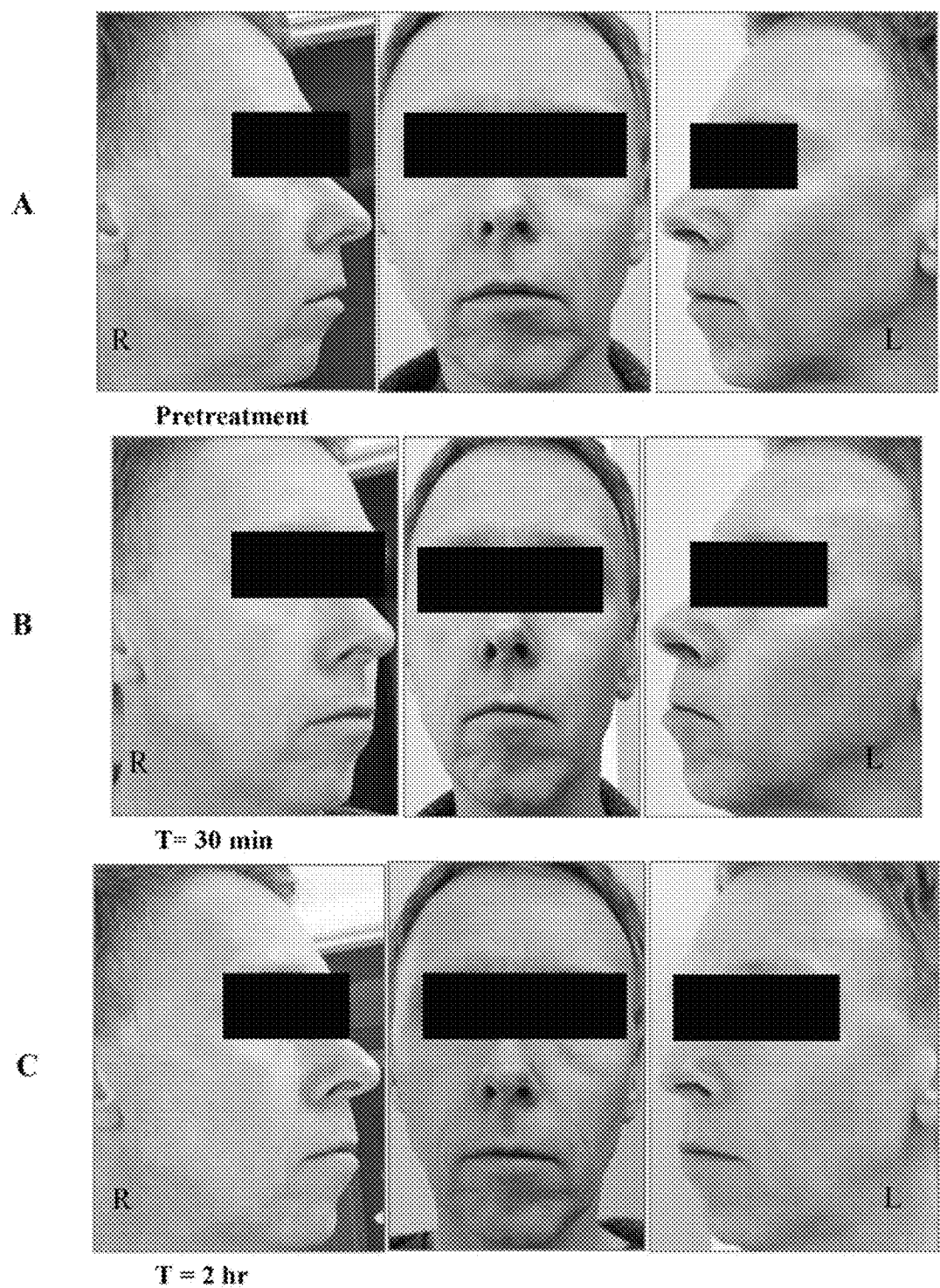
FIGS. 7A-7I: Representative photos from a bilateral trial of 0.10-0.15% brimonidine gel/0.010% capsaicin and an observation day. T=0 (pretreatment, FIG. 7A), T=30 min (FIG. 7B), T=2 hours (FIG. 7C), T=3.5 hours (FIG. 7D), T=5 hours (FIG. 7E), T=6 hours (FIG. 7F), T=7 hours (FIG. 7G), T=8 hours (FIG. 7H), and T=18-24 hours (FIG. 7I). At T=6 hours (FIG. 7F), mild superficial erythema developed bilaterally. Reapplication of 0.10-0.15% brimonidine gel/ 0.010% capsaicin to the right face resulted in resolution at T=7 hours (FIG. 7G). Application of 0.010% capsaicin alone to left face at T=7 hours resulted in resolution of superficial flushing at T=8 hours (FIG. 7H). Observation at T=18-24 hr (FIG. 7I) reveals no persistent patchy erythema and facial erythema is typical for baseline.
Figures 7D, 7E, 7F:
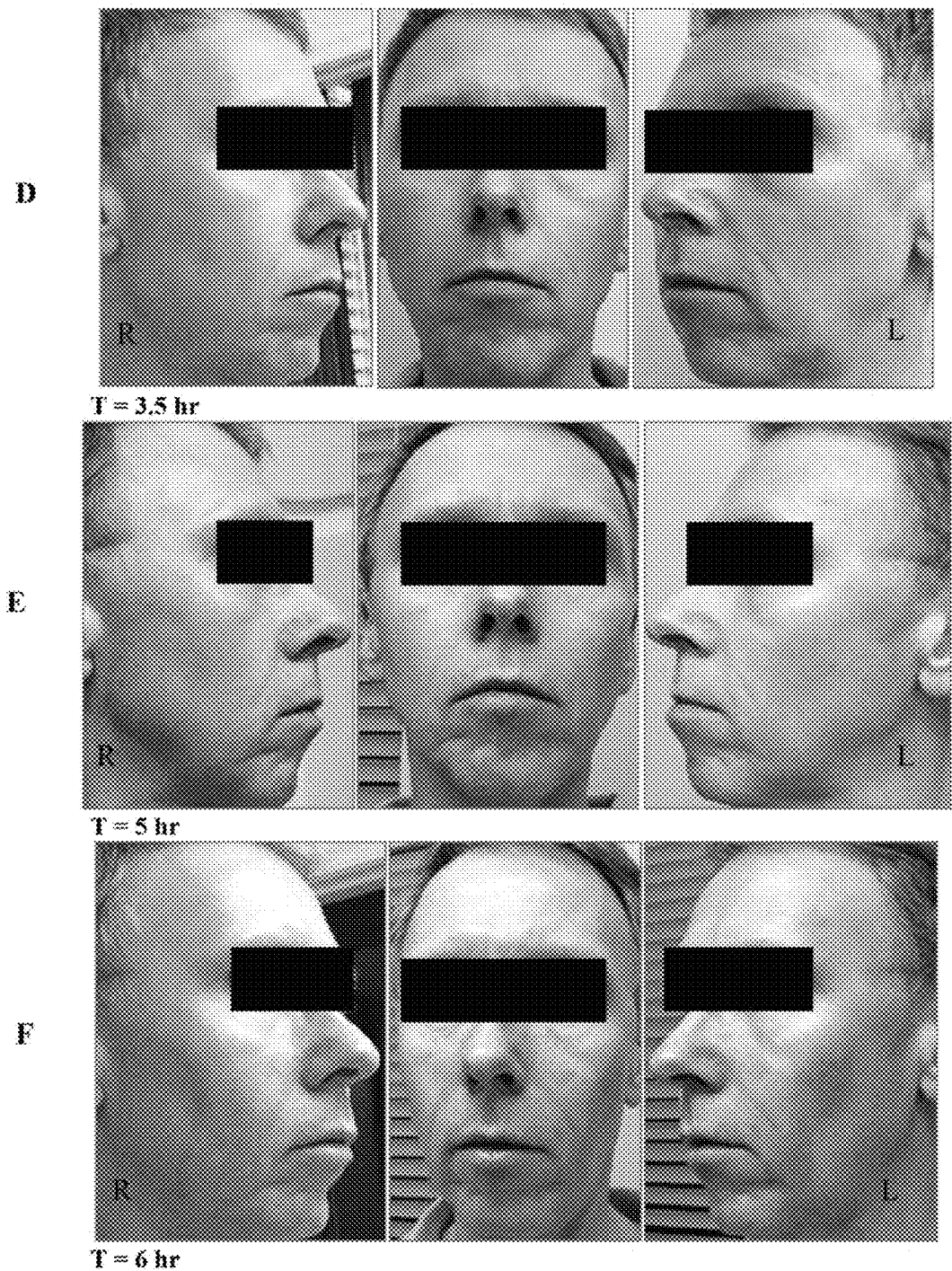
Figures 7G, 7H, 7I:
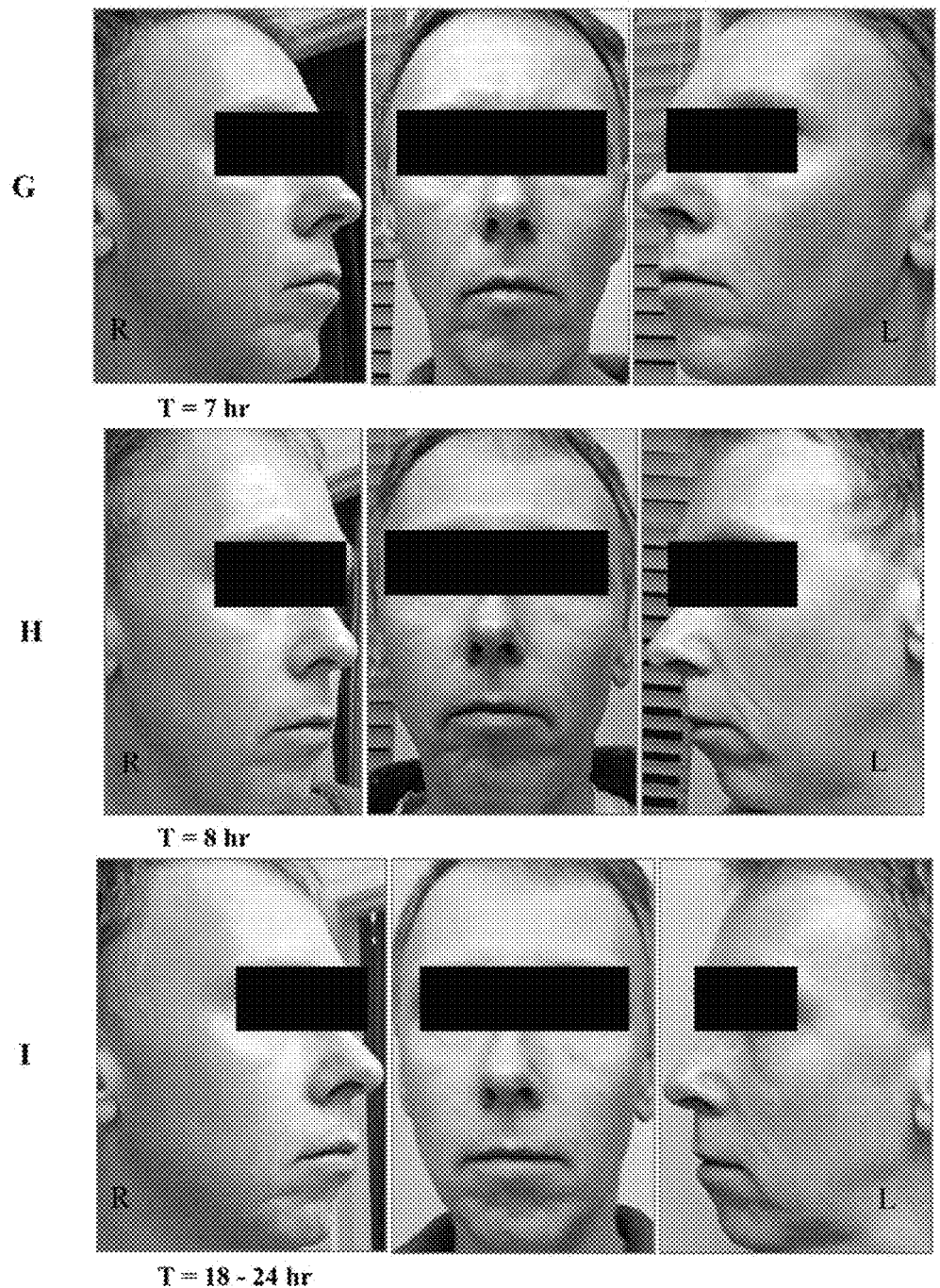

Treatment Day 1:
Pretreatment: Typical baseline erythema secondary to rosacea is present. Left and right side of face appear similar.
T=0: Burning sensation bilaterally within 1 minute of applying brimonidine/capsaicin mixture. Burning sensation resolved within 15 minutes. Erythema resolved within 30 minutes after application of brimonidine gel/capsaicin.
T=1 hr-8 hr: Erythema resolved bilaterally.
T=9 hr-10 hr: Superficially flushing affecting face bilaterally, No patchy erythema noted.
Treatment Day 2:
Pretreatment: Typical baseline erythema secondary to rosacea is present. Left and right side of face appear similar. No persistent, patchy erythema.
T=0: Burning sensation noted bilaterally within 1 minute of applying the brimonidine/capsaicin mixture. Burning sensation resolved within 15 minutes. Erythema resolved within 30 minutes after application of brimonidine gel/capsaicin.
T=1 hr-7 hr: Erythema resolved bilaterally.
T=: 8 hr-10 hr: Mild diffuse superficial flushing bilaterally, No persistent, patchy erythema.
Treatment Day 3:
Pretreatment: Typical baseline erythema secondary to rosacea is present. Left and right side of face appear similar. No persistent, patchy erythema.
Mild superficial flushing as combination wore off. No persistent, patchy erythema.
Treatment Day 4:
Pretreatment: Typical baseline erythema secondary to rosacea is present. Left and right sides of face appear similar. No persistent, patchy erythema (FIG. 5A).
T=0-30 min: Burning sensation noted bilaterally within 1 minute of applying brimonidine/capsaicin mixture. Burning sensation resolved within 15 minutes. Erythema resolved within 30 minutes after application of brimonidine gel/capsaicin (FIG. 5B).
T=1 hr-6 hr: Erythema resolved bilaterally (FIGS. 5C, 5D). No flushing. No persistent, patchy erythema bilaterally.
T=8 hr: Erythema slowly reappearing to baseline levels (FIG. 5E). No flushing. No persistent, patchy erythema.
Observation Days 1-4:
Typical baseline erythema secondary to rosacea is present throughout the day. Left and right side of face appear similar. No persistent, patchy erythema noted (FIG. 5F).
In summary, a combination of 0.020-0.025 wt % capsaicin and 0.20-0.25 wt % brimonidine was clinically effective and prevented development of persistent patchy erythema during a 4-day trial followed by 4 days of observation. Prior to application of brimonidine/capsaicin on each treatment day, the subject's diffuse facial erythema did not appear to be significantly different than typical baseline levels.
Comparison of 0.20-0.25 wt % Brimonidine/Vehicle with 0.20-0.25 wt % Brimonidine/0.020-0.025 wt % Capsaicin Cream
Differences in the development of persistent patchy erythema between the 0.20-0.25% brimonidine gel/vehicle and 0.20-0.25% brimonidine gel/0.020-0.025% capsaicin trials were compared at equivalent time points for the two groups (FIGS. 6A and 6B). It is apparent that addition of capsaicin to brimonidine gel (FIG. 6B) prevented the development of persistent patchy erythematous changes and allowed the face to return to baseline levels of erythema between treatment applications compared to brimonidine gel alone (FIG. 6A).
0.10-0.15% Brimonidine Gel/0.01% Capsaicin Cream (Lower Concentration Combination)
In order to determine whether a lower concentration of brimonidine gel/capsaicin cream was also effective and comfortable, two separate single day trials were conducted wherein the test subject's face was treated bilaterally with 0.10-0.15 wt % brimonidine gel/0.01 wt % capsaicin cream combination. At the end of each treatment day, the subject's face was treated with 0.01 wt % capsaicin alone. Results are shown in FIGS. 7A-7I and summarized below.
Treatment Day:
Pretreatment: Typical baseline erythema present bilaterally.
T=0: Mild warmth upon application of 0.10-0.15 wt % brimonidine gel/0.01 wt % capsaicin cream combination. No burning or pain noted.
T=15 min: Mild erythema and flushing. No discomfort.
T=30 min-5 hr: Erythema and flushing resolved bilaterally (FIGS. 7B-7E).
T=6 hr; Mild superficial rebound-type flushing noted bilaterally (FIG. 7F). 0.10-0.15 wt % brimonidine gel/0.01 wt % capsaicin cream combination reapplied to right face.
T=7 hr: Flushing/erythema resolved on right face 1 hour after reapplication of brimonidine/capsaicin (FIG. 7G). Flushing was still present on left face. 0.01% capsaicin cream alone was applied to left face.
T=8 hr: Flushing/erythema resolved on left face following application of 0.010 wt % capsaicin alone (FIG. 7H). Right face also without superficial flushing or erythema 2 hours after reapplication of 0.10-0.15 wt % brimonidine gel/0.01 wt % capsaicin cream combination.
Observation Day:
T=18-24 hr: Typical baseline level bilaterally (FIG. 7I). No persistent, patchy erythema or flushing noted bilaterally.

This trial (bilateral 0.10-0.15 wt % brimonidine/0.01 wt % capsaicin) was repeated and results shown below.

Treatment Day:

Pretreatment: Typical baseline erythema present bilaterally.

T=0: Mild warmth upon application of 0.10-0.15% brimonidine gel/0.01% capsaicin cream combination. No burning or pain noted.

T=15 min: Mild erythema and flushing. No discomfort.

T=30 min-5 hr: Erythema and flushing resolved bilaterally. Similar to brimonidine gel alone.

T=8 hr: Mild superficial rebound-type flushing noted bilaterally. 0.01% capsaicin cream applied bilaterally at T=8 hr.

Observation Day:

T=18-24 hr: Typical diffuse baseline erythema present bilaterally. No persistent, patchy erythema or flushing noted bilaterally.

Table 5 shows the CEA grading after topical application of the 0.10-0.15 wt % brimonidine/0.010-0.015 capsaicin formulations.

TABLE 5

CEA grading after administration of 0.10-0.15 wt % brimonidine/0.010 wt % capsaicin formulation

| Formulations, Time after administration | CEA Score | Observations |
|---|---|---|
| Baseline (FIG. 7A) | 2 | Mild baseline erythema with definite redness |
| 0.10-0.15% brimonidine/0.010 capsaicin, 30 min (FIG. 7B) | 1 (about a 1-grade improvement within about 20 minutes or about 30 minutes as evaluated by CEA) | Gradual and marked decrease in erythema and redness noted by t = 20 min. Skin is almost clear with only slight redness. Stable at t = 30 min (photo). |
| 0.10-0.15% brimonidine/0.010 capsaicin, 2 hours (FIG. 7C) | 0 (about a 2-grade improvement within about 1 hour as evaluated by CEA) | (Gradual and complete resolution of erythema achieved by t = 1 hr. Clear skin with no signs of erythema. Persisted stable CEA = 0 until photo at t = 4 hr. |
| 0.10-0.15% brimonidine/0.010 capsaicin, 3.5 hours (FIG. 7D) | 0 | Continued clear skin with no signs of erythema, stable at t = 3.5 hr |
| 0.10-0.15% brimonidine/0.010 capsaicin 5 hours (FIG. 7E) | 1 | Gradual return of mild erythema with slight redness noted between t = 4 hr and t = 5 hr. Skin is almost clear with only slight redness. Photo at t = 5 hr. |
| 0.10-0.15% brimonidine/0.010 capsaicin, 6 hours (Reapplication of 0.10-0.15% brimonidine/0.010% capsaicin to right face at T = 6 hours) (FIG. 7F) | 3 | Rapid return of superficial erythema and redness between t = 5 hr and t = 6 hr. Photo at t = 6 hr. |
| 0.10-0.15% brimonidine/0.010 capsaicin, 7 hours (Application of 0.010% capsaicin alone to left face at T = 7 hr) (FIG. 7G) | Right face: 1 (about a 2-grade improvement within about 1 hour as evaluated by CEA) Left face: 3 | Right face: Gradual decrease in erythema and redness on right face between t = 6 hr and t = 7 hr after reapplication of 0.10-0.15% brimonidine/0.010% capsaicin. Skin is almost clear with only slight redness. Photo at t = 7 hr. Left face: Moderate erythema with marked redness present on left face between t = 6 hr and t = 7 hr. Photo at t = 7 hr. |
| 0.10-0.15% brimonidine/0.010 capsaicin, 8 hours (FIG. 7H) | Right face: 0 (about a 3-grade improvement within about 2 hours as evaluated by CEA) Left face: 1 (about a 2-grade improvement within about 1 hour as evaluated by CEA) | Right face: Gradual and complete resolution of erythema and redness on right face between t = 7 hr and t = 8 hr. Clear skin with no signs of erythema. Photo at t = 8 hr. Left face: Gradual resolution of erythema and redness of left face between t = 7 hr and t = 8 hr. Skin is almost clear with only slight redness. Photo at t = 8 hr. |

TABLE 5-continued

CEA grading after administration of 0.10-0.15 wt % brimonidine/0.010 wt % capsaicin formulation

| Formulations, Time after administration | CEA Score | Observations |
|---|---|---|
| 0.10-0.15% brimonidine/0.010 capsaicin, 18-24 hours (FIG. 7I) | 1 | Mild baseline bilateral erythema with slight redness between t = 18 and 24 hr. |

In summary, addition of 0.01% capsaicin cream to 0.10-0.15% brimonidine gel was clinically effective and prevented the development of persistent patchy erythema. The mixture was well tolerated and produced only a transient (a few minutes) mild sensation of warmth. Reapplication of the mixture was effective in rapidly decreasing the transient superficial flushing that can occur as the effects of brimonidine subside over several hours. No sequelae or patchy erythema were noted the following day and the subject's facial erythema had returned to a quiet baseline.

CONCLUSION

Combining topical brimonidine with capsaicin prevents the patchy cutaneous erythema that has been observed as a side effect of brimonidine gel use. In order to improve patient tolerance and reduce side effects, the currently approved brimonidine tartrate gel can be reformulated at a lower brimonidine concentration (about 0.10 wt % to about 0.25 wt %) and be combined with capsaicin (about 0.005 wt % to about 0.015 wt %). This study demonstrates that the combination of topical brimonidine and capsaicin is clinically efficacious, non-irritating, and prevents the development of persistent patchy erythema (rebound erythema) associated with repeated applications of brimonidine.

DISCUSSION

This study presents evidence that the application of topical capsaicin combined with brimonidine helps to prevent some side effects, particularly persistent patchy erythema (rebound erythema). Additionally, the present study finds that incorporation of capsaicin along with topical brimonidine gel, as well as low concentration capsaicin used alone (e.g., before bed), allows the facial skin to reliably reestablish its baseline state. Addition of capsaicin was not observed to alter the clinical onset, effectiveness or duration of action of topical brimonidine gel.
Capsaicin Cream The first set of experiments was performed to determine the tolerability of topically applied capsaicin cream. It was determined that 0.1 wt % capsaicin produced prolonged, almost intolerable burning and pain. Its effects were apparent even 24 hours after application. Decreasing the concentration to 0.025 wt % or 0.020 wt % still resulted in only a transient burning sensation, however, the erythematous flushing induced by this concentration alone was still apparent several hours after application. Capsaicin cream at a concentration of ~0.010-0.015 wt % produced a transient (few minutes) warmth and mild erythema that resolved by 15-30 minutes post-application.
Brimonidine Gel/Vehicle To establish a baseline response to brimonidine gel alone, a 3-day trial of bilaterally applied 0.20-0.25 wt % brimonidine gel/vehicle was performed. Within 24 hours of the first application of brimonidine gel, persistent patchy erythema developed bilaterally and worsened throughout the trial. Initially, the patchy erythema started in the buccal areas but progressed to include the forehead and temporal areas by the end of the trial.
Brimonidine Gel/Capsaicin Cream In order to determine the effects of capsaicin on the development of persistent, patchy erythema, 0.20-0.25 wt % brimonidine gel/0.020-0.025 wt % capsaicin was applied once daily over the course of 4 days in a separate trial. Each evening, the subject's face was treated with 0.025% capsaicin. Prior to treatment each morning during the trial, both sides of the subject's face had returned to pretreatment baseline levels and no persistent patchy erythema was noted. No difference in the onset of clinical effectiveness of brimonidine gel/capsaicin cream vs. brimonidine gel alone (assessed from previous experience) could be discerned by 30 min post-application. There was also no difference noted in the duration of effectiveness of brimonidine gel. Similar to brimonidine gel alone, both sides of the subject's face occasionally developed periodic episodes of transient, superficial flushing as the effects of the brimonidine wore off at the end of the day, however, at no time during the trial did persistent, patchy erythema occur.

The subject's face was observed for 4 days after the end of the trial. During this time, facial erythema was assessed to be at typical baseline levels. Patchy erythema did not develop. The results of this trial indicate that the addition of capsaicin to brimonidine gel prevents the development of persistent, patchy erythema that can occur as a side effect of brimonidine use.

Side by side comparison of the brimonidine gel/vehicle and brimonidine gel/capsaicin trials (FIG. 6) demonstrates the significant effects of capsaicin in preventing persistent patchy erythema.
Lower Concentration Brimonidine Gel/Capsaicin Cream Because the concentration of capsaicin used in the previous trial was high enough to induce a moderate but transient burning sensation, a single day trial using lower concentrations of both brimonidine (0.10-0.15 wt %) and capsaicin (0.01 wt %) was conducted. This low concentration of capsaicin alone produced a sensation of warmth without burning and a mild, transient (~15 min) flushing. Additionally, the concentration of brimonidine was lowered to 0.10-0.15 wt % which was better tolerated and similar to, or as efficacious as, higher concentrations of brimonidine. Facial erythema was completely resolved within 30 minutes following application of 0.10-0.15 wt % brimonidine gel/0.01 wt % capsaicin cream combination. Six hours after application, mild superficial erythematous flushing was noted on the subject's face bilaterally. At T=6 hr, 0.10-0.15 wt % brimonidine gel/0.01 wt % capsaicin cream was reapplied to the right face, vehicle was applied to the left face and the effects were assessed at T=7 hr. At T=7 hr, the right facial flushing was completely resolved whereas the left face remained flushed. At this point, 0.01% capsaicin alone was applied to the left face and the results were reassessed at T=8 hr. Interestingly, at T=8 hr, the superficial flushing of the left face had resolved after application of capsaicin alone. At T=8 hr, the right face, now 2 hours after re-application of the combination of brimonidine/capsaicin, also remained free of erythema.

Observational photos obtained at T=18-24 hr revealed typical baseline erythema and no evidence of persistent, patchy erythematous changes. This trial provides further evidence that addition of capsaicin to brimonidine gel prevents the development of persistent, patchy erythema (rebound erythema). Additionally, lower concentration brimonidine gel/capsaicin cream is effective and well tolerated for re-application to treat transient, superficial flushing. Flushing was resolved after the application of low concentration 0.01 wt % capsaicin alone supports the hypothesis that capsaicin works quickly and effectively to reverse erythema and/or flushing when used in conjunction with a topical alpha adrenergic agonist.

When used alone (i.e., in the absence of capsaicin), 0.20-0.25 wt % brimonidine gel caused the development of persistent, patchy facial erythema within 24 hours of application (FIG. 4). These patchy erythematous changes worsened and persisted throughout the trial. The addition of 0.020-0.025 wt % capsaicin to 0.20-0.25 wt % brimonidine gel helped to prevent the rebound erythema from occurring. However, 0.20-0.25 wt % of capsaicin caused a transient burning sensation upon application.

Further reduction of the brimonidine gel concentration to 0.10-0.15 wt % produced no clinically apparent difference with regard to latency of onset or duration of effectiveness. When combined with 0.010 wt % capsaicin, this formulation was clinically efficacious, comfortable and resulted in no persistent patchy erythema. Additionally, reapplication of this concentration after 6-8 hours was well tolerated and produced clinically favorable results, again with no persistent patchy erythema. Of note, it was found that application of low concentration (about 0.005 to 0.02 wt %, about 0.006 to 0.015 wt %, or about 0.008 to 0.012 wt %) capsaicin alone to areas exhibiting superficial flushing as the effects of brimonidine subside, acted to reverse the flushing reaction. This reversal was apparent at least within one hour after application (the total duration of effectiveness was not followed).

This study demonstrates that about 0.10% to about 0.25 wt % topical brimonidine in combination with about 0.005 wt % to 0.015 wt % capsaicin can help prevent rebound erythema (or persistent patchy erythema) and could be safely reapplied to treat early superficial rebound erythema as needed. It may be administered once a day, twice a day, three times a day, more times a day, or as needed.

In addition to using a combination of capsaicin and brimonidine, a low concentration capsaicin (e.g., about 0.005 to 0.02 wt %, about 0.006 to 0.015 wt %, or about 0.008 to 0.012 wt %) may be applied at a time separate from administering a combination of capsaicin and brimonidine (e.g., at the end of the day or at night). In addition to preventing the development of rebound erythema (patchy erythematous changes), capsaicin has been shown to reverse early rebound erythema and/or flushing.

REFERENCES

Anand P, Bley K, Topical capsaicin for pain management: therapeutic potential and mechanisms of action of the new high-concentration 8% patch, *Br J Anesth*. 2011, 107(4): 490-502

Andoh T, Kuraishi Y, Nitric oxide enhances substance P-induced itch-associated responses in mice, *Br J Pharmacol*. 2003, 138(1):202-208

Bouvier G, Learn D B, Nonne C, et al, Protective effect of dermal brimonidine applications against UV radiation-induced skin tumors, epidermal hyperplasia and cell proliferation in the skin of hairless mice, *Photochem Photobiol*. 2015, 91(6):1479-1487

Bull H A, Hothersall J, Chowdhury N, et al, Neuropeptides induce release of nitric oxide from human dermal microvascular endothelial cells, *J Invest Dermatol*. 1996, 106 (4):655-660

Charkoudian N, Mechanisms and modifiers of reflex induced cutaneous vasodilation and vasoconstriction in humans, *J Appl Physiol*. 1985, 109(4):1221-1228

Chu M B, Garrett S, Siegfried E, Efficacy of topical brimonidine-timolol for haemangioma of infancy and perils of off-label prescribing, *BMJ Case Rep.* 2013; 2013bcr2013009365.doi:10.1136/bcr-2013-009365

Del Bianco E, Geppetti P, Zippi P, et al, The effects of repeated dermal application of capsaicin to the human skin on pain and vasodilation induced by intraderma injection of acid and hypertonic solutions, *Br J Clin Pharmacol*. 1996, 41(1):1-6

Ebertz J M, Hirshman C A, Kettelkamp N S, et al, Substance P-induced histamine release in human cutaneous mast cells, *J Invest Dermatol*. 1987, 88:682.685

Fowler J, Jarratt M, Moore A, et al, Once daily topical brimonidine tartrate gel 0.5% is a oval treatment for moderate to severe facial erythema of rosacea: results of two multicentre, randomized and vehicle-controlled studies, *Br J Dermatol*. 2012, 166(3):633-641

Gamse R, Holzer P, Lembeck F, Decrease of substance P in primary afferent neurons and impairment of neurogeic plasma extravasation by capsaicin, *Br J Pharmacol*. 1980, 68:207-213

Gerber P A, Topical brimonidine tartrate gel 0.33% effectively reduces the post treatment erythema of daylight-activated photodynamic therapy, Br J Dermatol. 2016, Jan. 3, Epub.

Jackson J M, Fowler J, Moore A, et al, Improvement in facial erythema within 30 minutes of initial application of brimonidine tartrate in patients with rosacea, *J Drugs Dermatol*. 2014, 13(6):699-704

Kellogg D L, In vivo mechanisms of cutaneous vasodilation and vasoconstriction in humans during thermoregulatory challenges, *J Applied Physiol*. 20015, 100(5):1709-1718

Nolano M, Simone D A, Wendelschafer-Crabb G, et al, Topical capsaicin in humans: parallel loss of epiderma nerve fibers and pain sensation, *Pain*. 1999, 81(1):135-145

Peppin J F, Pappagallo M, Capsacinoids in the treatment of neuropathic pain: a review, *Ther Adv Neurol Disord*. 2014, 7(1):22-32

Reinholz M, Heppt M, Tietze J K, et al, Photoletter to the editor: Topical 0.5% brimonidine gel to camouflage redness of immature scars, *J Dermatol Case Rep*. 2015 9(3):87-88

Repke H, Bienert M, Mast cell activation—a receptor-independent mode of substance P action? *FEBS Lett.* 1987, 221(2):236-240

Schleichert R, Weiss E, Topical brimonidine gel as a hemostatic agent after dermatologic surgery, *Dermatol Surg.* 2015, 41(7):872-873

Van Gerven L, Alpizar Y A, Wouters M M, et al, Capsaicin treatment reduces nasal hyperreactivity and transient receptor potential cation channel subfamily V, receptor 1

(TRPV1) overexpression in patients with idiopathic rhinitis, *Allergy Clin Immunol.* 2014, 133(5):1332-1339

Wong B J, Tublitz N J, Minson C T, Neurokinin-1 receptor desensitization to consecutive microdialysis infusions of substance P in human skin, *J Physiol.* 2005, 563(Pt 3): 1047-1056

Wong B J, Minson C T, Neurokini-1 receptor desensitization attenuates cutaneous active vasodilation in humans, *J Physiol.* 2006, 577.3:1043-1051

Wong B J, Minson C T, Altered thermal hyperaemia in human skin by prior desensitization of neurokinin-1 receptors, *Exp Physiol.* 2011 6(6):599-609

Brimonidine tartrate for the treatment of injection related erythema (BRITE), Clinical Trials.gov Identifier: NCT02568111.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method of treating or preventing rebound erythema, the method comprising topically applying an effective amount of an alpha-adrenergic agonist and an effective amount of a capsaicinoid to an affected area of the skin of a subject.

2. The method of claim 1, wherein the rebound erythema is associated with a topical alpha-adrenergic agonist.

3. The method of claim 1, wherein the alpha-adrenergic agonist and the capsaicinoid are applied simultaneously.

4. The method of claim 1, wherein the capsaicinoid is applied prior to, or after, the application of the alpha-adrenergic agonist.

5. The method of claim 1, wherein the capsaicinoid and the alpha-adrenergic agonist are in a composition.

6. The method of claim 1, wherein the capsaicinoid and the alpha-adrenergic agonist are in two separate compositions.

7. The method of claim 1, wherein the casaicinoid is selected from the group consisting of capsaicin, dihydrocapsaicin, nordihydrocapsaicin, homodihydrocapsaicin, homocapsaicin, noninvamide, and combinations thereof.

8. The method of claim 1, wherein the alpha-adrenergic agonist is selected from the group consisting of brimonidine, oxymetazoline, tetrahydrozoline, nephazoline, xylometazoline, phenylepherine, methoxamine, mephentermine, metaraminol, desglymidodrine, midodrine, salts thereof, and combinations thereof.

9. A method of treating or preventing rebound erythema, the method comprising topically applying a pharmaceutical composition comprising an effective amount of a capsaicinoid to an affected area of the skin of a subject, wherein the area is affected by the rebound erythema associated with a topical alpha-adrenergic agonist.

* * * * *